US006174881B1

(12) United States Patent
Borer et al.

(10) Patent No.: US 6,174,881 B1
(45) Date of Patent: Jan. 16, 2001

(54) HYDROXYMETHYLIMIDAZODIAZEPINES AND THEIR ESTERS

(75) Inventors: René Borer, Reinach (CH); Bernd Büttelmann, Schopfheim (DE); André Szente, Riehen (CH); Max Gerecke-Jecklin, deceased, late of Reinach (CH); by Ruth Elisabeth Gerecke-Jecklin, executor, Reinach (CH); by Peter Eduard Gerecke-Szuran, executor, Riehen (CH); by Andreas Christian Gerecke, executor, Reinach (CH); by Silvia Ursula Striebel-Gerecke, executor, Münchenstein (CH)

(73) Assignee: Hoffman-La Roche Inc., Nutley, NJ (US)

( * ) Notice: Under 35 U.S.C. 154(b), the term of this patent shall be extended for 0 days.

(21) Appl. No.: 08/860,785

(22) PCT Filed: Jan. 3, 1996

(86) PCT No.: PCT/CH96/00001

§ 371 Date: Sep. 4, 1997

§ 102(e) Date: Sep. 4, 1997

(87) PCT Pub. No.: WO96/20941

PCT Pub. Date: Jul. 11, 1996

(30) Foreign Application Priority Data

Jan. 6, 1995 (CH) .......................................... 28/95

(51) Int. Cl.[7] ....................... A61K 31/551; C07D 243/06
(52) U.S. Cl. ............................. 514/220; 540/562
(58) Field of Search .............................. 514/220; 540/562

(56) References Cited

U.S. PATENT DOCUMENTS

| 3,763,179 | * 10/1973 | Gall ........................................ 260/309 |
| 4,280,957 | 7/1981 | Walser, et al. ..................... 260/244.4 |
| 4,621,083 | * 11/1986 | Casals-Stenzel et al. ........... 514/220 |
| 4,902,794 | 2/1990 | Hester, Jr. ............................ 540/563 |

FOREIGN PATENT DOCUMENTS

| 25 47 652 | * 5/1976 | (DE) . |
| 2233483 | 1/1973 | (EP) . |
| 0 139 460 | 5/1985 | (EP) . |
| WO 95/14472 | 6/1995 | (WO) . |
| WO 95/14694 | 6/1995 | (WO) . |

OTHER PUBLICATIONS

J. Med. Chem. 1971, vol. 14, No. 11 pp. 1078–1081.
J. Am. Chem. Soc. 1953, vol. 75, pp. 6244–6249.
J. Chem. Res. Synop. 1980, p. 400.
J. Med. Chem. 1991, vol. 34, pp. 1209–1221.
J. Med. Chem. 1980, vol. 23, pp. 392–402.
Nature vol. 294, pp. 763–765, 1981.
J. Neurochemistry vol. 37, pp. 714–722, 1981.
Carbohyd. Res. 1969, vol. 10, pp. 35–48.
Commun. 1993, vol. 23, pp. 985–992.
Abstract corresponding to DE 2233483, 1973.

* cited by examiner

Primary Examiner—Mukund J. Shah
Assistant Examiner—Brenda Coleman
(74) Attorney, Agent, or Firm—George W. Johnston; Patricia S. Rocha-Tramaloni; Robert A. Silverman

(57) ABSTRACT

The invention is concerned with hydroxymethyl-imidazodiazepines and their esters of general formula I. These compounds can be used as anxiolytic and/or anticonvulsant and/or muscle relaxant and/or sedative-hypnotic active substances.

18 Claims, No Drawings

HYDROXYMETHYLIMIDAZODIAZEPINES AND THEIR ESTERS

The present invention is concerned with hydroxymethylimidazodiazepines and their esters of the general formula

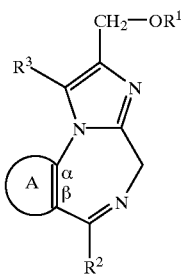

I wherein A and the two carbon atoms denoted by α and β together signify one of the residues

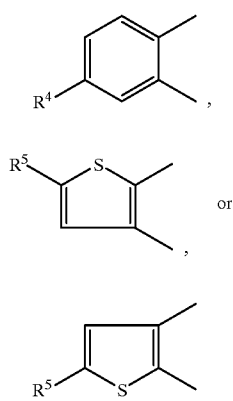

$R^1$ signifies hydrogen or lower-alkanoyl;
$R^2$ signifies phenyl, o-halophenyl or 2-pyridyl;
$R^3$ signifies hydrogen, lower-alkyl, methylaminomethyl, allylaminomethyl or diethylaminomethyl;
$R^4$ signifies halogen, $CF_3$ or nitro;
$R^5$ signifies hydrogen or halogen,
as well as pharmaceutical acceptable salts thereof.

These compounds and salts are novel and have valuable pharmacodynamic properties. They are therefore suitable for therapeutic purposes, especially for anxiolytic and/or anticonvulsant and/or muscle relaxant and/or sedative-hypnotic purposes. A particular advantage of the novel compounds of general formula I is the good water solubility of their salts as well as a short duration of action for the uses referred to above.

Objects of the present invention are the mentioned compounds of formula I and salts thereof per se and as therapeutically active substances, their manufacture and their use for therapeutic purposes and, respectively, for the production of corresponding medicaments as well as medicaments containing a compound of formula I or a salt thereof and the production of such medicaments.

The term "lower" denotes residues or compounds with a maximum of 7, preferably a maximum of 4, carbon atoms. The term "alkyl" denotes straight-chain or branched saturated hydrocarbon residues, such as methyl, ethyl, n-propyl, iso-propyl, n-butyl, sec.-butyl, iso-butyl and tert.-butyl. The term "alkenyl" denotes straight-chain or branched hydrocarbon residues which contain a C—C double bond, such as allyl, but-2-enyl, 3-methyl-but-2-enyl and the like. The term "halogen" embraces fluorine, chlorine, bromine and iodine. The term "amino" denotes residues such as $NH_2$, NH-lower-alkyl, N-di-loweralkyl, NH-lower-alkenyl, morpholino, piperidino, pyrrolidin-1-yl, methylpiperiazin-1-yl and the like. The term "alkanoyl" denotes residues such as acetyl, propionyl and the like.

When A in formula I signifies a residue of formula $A^1$, there are preferred those compounds in which $R^1$ signifies hydrogen, $R^2$ signifies o-fluoro- or o-Cl-phenyl, $R^3$ signifies hydrogen or allylaminomethyl and $R^4$ iodine or chlorine.

The following compounds are examples of these:
8-Chloro-6-(2-fluorophenyl)-4H-imidazo[1,2-a] benzodiazepine-2methanol;
1-allylaminomethyl-8-chloro-6-(2-fluorophenyl)-4H-imidazo[1,2-a][1,4]benzodiazepine-2-methanol;
8-chloro-6-(2-chlorophenyl)-4H-imidazo[1,2-a][1,4] benzodiazepine-2-methanol;
8-iodo-6-(2-fluorophenyl)-4H-imidazo[1,2-a][1,4] benzodiazepine-2-methanol.

When A in formula I signifies a residue of formula $A^2$, there are preferred those compounds in which $R^1$ signifies hydrogen or carbonylmethyl, $R^2$ signifies o-fluorophenyl, $R^3$ signifies hydrogen and $R^5$ signifies chlorine.

The following compounds are examples of these:
2-Chloro-4-(2-fluorophenyl)-8,9-dihydro-6H-imidazo[1,2-a]thieno[3,2-f][1,4]diazepine-8-methanol;
methyl[2-chloro-4-(2-fluorophenyl)-8,9-dihydro-6H-imidazo[1,2-a]thieno[3,2-f]diazepin-8-yl]acetate.

The compounds of general formula I mentioned earlier and their pharmaceutically acceptable acid addition salts can be manufactured in accordance with the invention by a) converting compounds of the general formulae

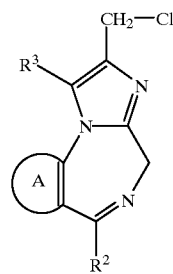

IIa with a basic reagent into compounds of the general formula

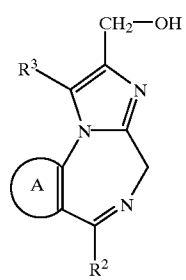

Ia wherein A, $R^2$ and $R^3$ have the above significance, or b) converting compounds of general formula Ia or IIa into compounds of the general formula

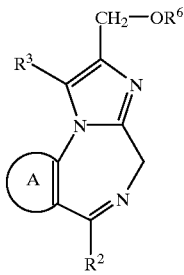

Ib wherein A, R² and R³ have the above significance and R⁶ signifies lower-alkanoyl, or c) hydrolyzing compounds of general formula Ib to compounds of general formula Ia, or d) reducing compounds of the general formula

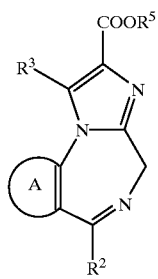

III wherein A, R² and R³ have the above significance and R⁵ signifies lower-alkyl, to compounds of the general formula Ia or e) cleaving off the protecting group from a compound of the general formula

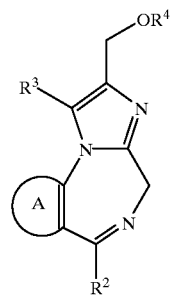

IV wherein A and R² and R³ have the above significance and R⁴ signifies a protecting group, or f) cyclizing compounds of the general formula

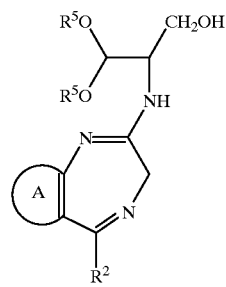

V wherein A and R² have the above significance and R⁵ signifies lower-alkyl, in an acidic medium to compounds of general formula I in which R³ signifies hydrogen, and g) if desired, converting a compound of general formula I into a pharmaceutically usable acid addition salt.

Compounds of general formula Ia can be manufactured according to process variant a) by treating compounds of formulae IIa with a basic reagent. This is conveniently carried out as follows: a compound of formula IIa is stirred under a protective gas atmosphere for several hours in an alkali hydroxide solution, preferably in sodium hydroxide, or treated with sodium hydrogen carbonate and subsequently worked up according to known methods.

Compounds of general formula Ib are obtained in accordance with process variant b) starting from compounds of formula Ia by reacting these compounds conveniently with acetic anhydride or the like in the presence of strong acid, for example perchloric acid, or starting from a compound of formula IIa by reacting this with sodium acetate or the like. These methods will be familiar to any person skilled in the art.

The compounds of general formula Ib are hydrolyzed to compounds of general formula Ia according to process variant c). This is conveniently effected with a methanolic sodium methanolate solution.

Compounds of formula Ia are obtained in accordance with process variant d). This is effected by reducing a compound of general formula III with a suitable reducing agent, for example with a lithium aluminum hydride solution. This is conveniently carried out as follows: the reducing agent is dissolved in a suitable organic solvent, for example tetrahydrofuran, cooled to about −70 to −80° C. and treated with a solution of a compound of general formula III. After a reaction period of about 1 hour the mixture is warmed slowly to 0° C. and subsequently worked up according to usual methods.

Compounds of general formula Ia are obtained in accordance with process variant e). Suitable protecting groups and methods for their cleavage will be familiar to any person skilled in the art, although, of course, only those protecting groups can be used which can be cleaved off by methods under the conditions of which other structural elements in the compounds are not concomitantly effected. Compounds of general formula I in which $R^1$ signifies hydrogen and $R^3$ signifies aminomethyl and $R^2$ has the significance set forth above can be conveniently manufactured by converting a compound of general formula IVb which carries a protecting group into compounds of general formula Ia in one process step by treating the reactive compounds of formula IVb with a corresponding amine and by simultaneously cleaving off the protecting group by working in the acidic range. The following are especially preferred amines: diethylamine, morpholine, methylamine, allylamine and the like.

The compounds of formula I are converted into pharmaceutically acceptable acid addition salts in accordance with process variant g). Salts with both inorganic acids and organic acids come into consideration. Examples of such salts are the hydrochlorides, hydrobromides, sulphates, nitrates, citrates, acetates, maleates, succinates, methanesulphonates, p-toluenesulphonates and the like. These salts can be manufactured according to methods which are known per se and which will be familiar to any person skilled in the art.

The starting products of formulae Ia, III, IVb and V above can be prepared in accordance with Scheme 1 or 2 hereinafter.

In Schemes 1 and 2 A and $R^2$ have the significance set forth above, $R^5$ signifies lower-alkyl and $R^6$ signifies halogen.

SCHEME I

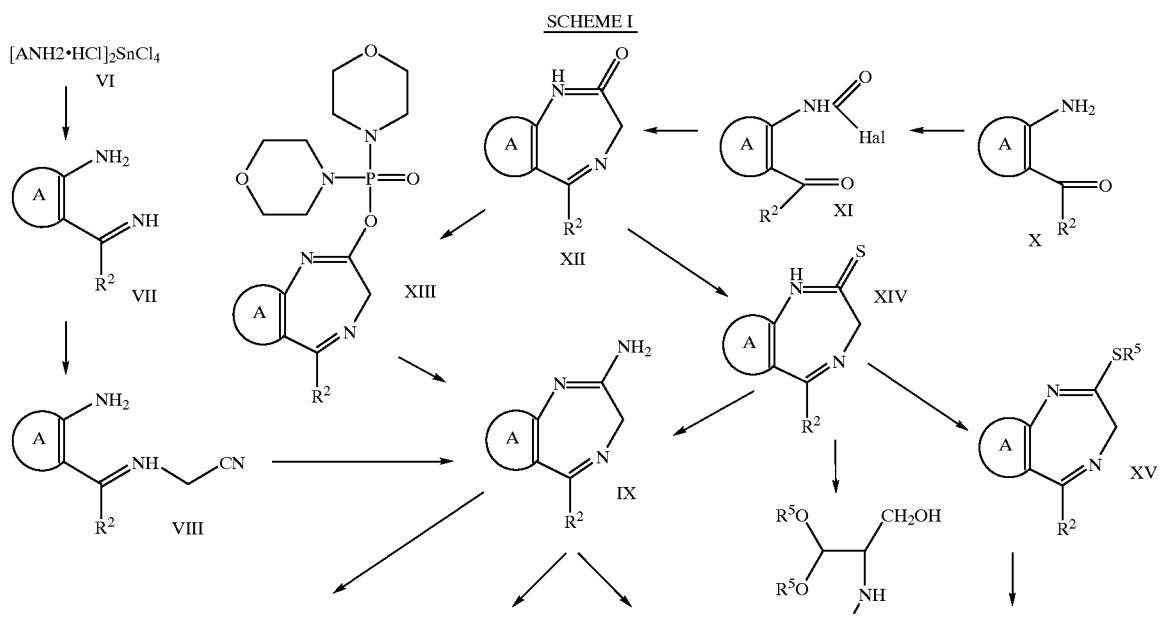

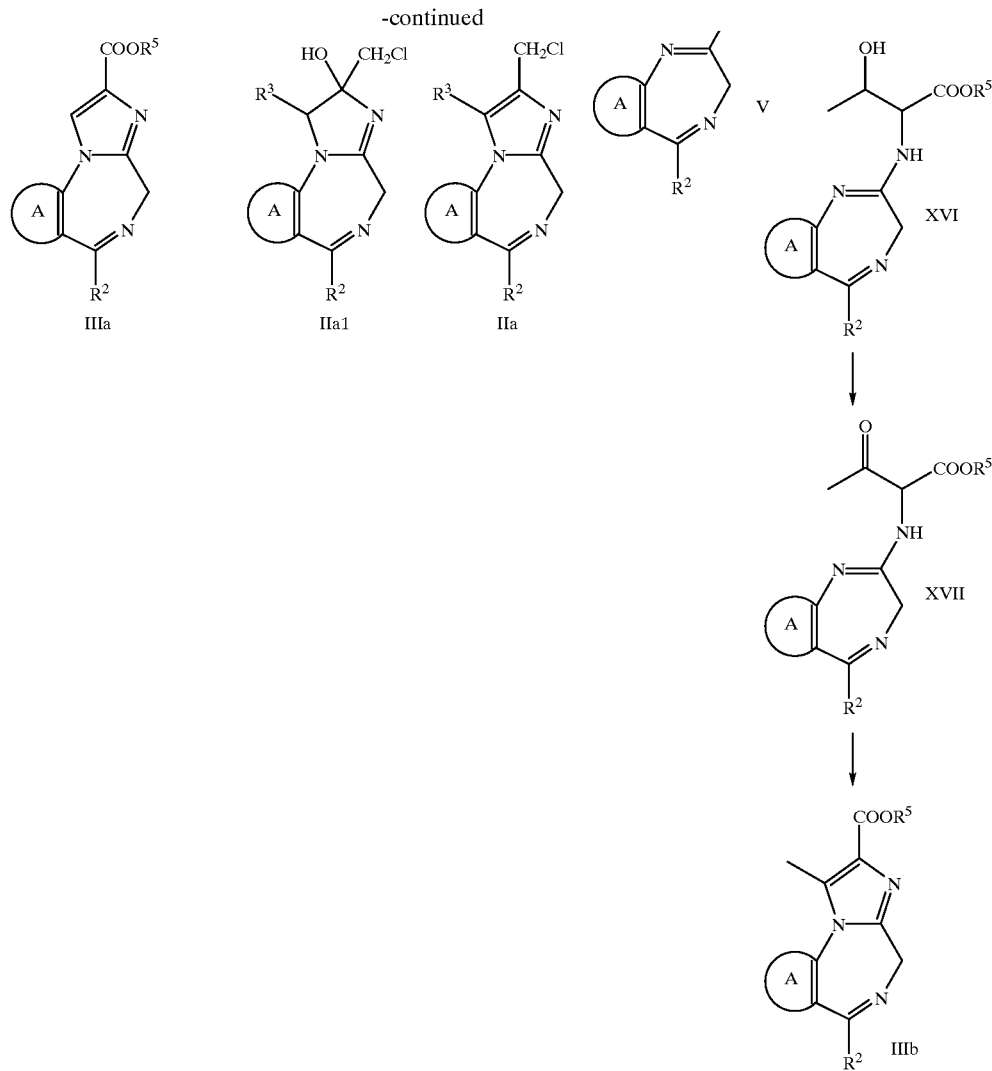
SCHEME 2
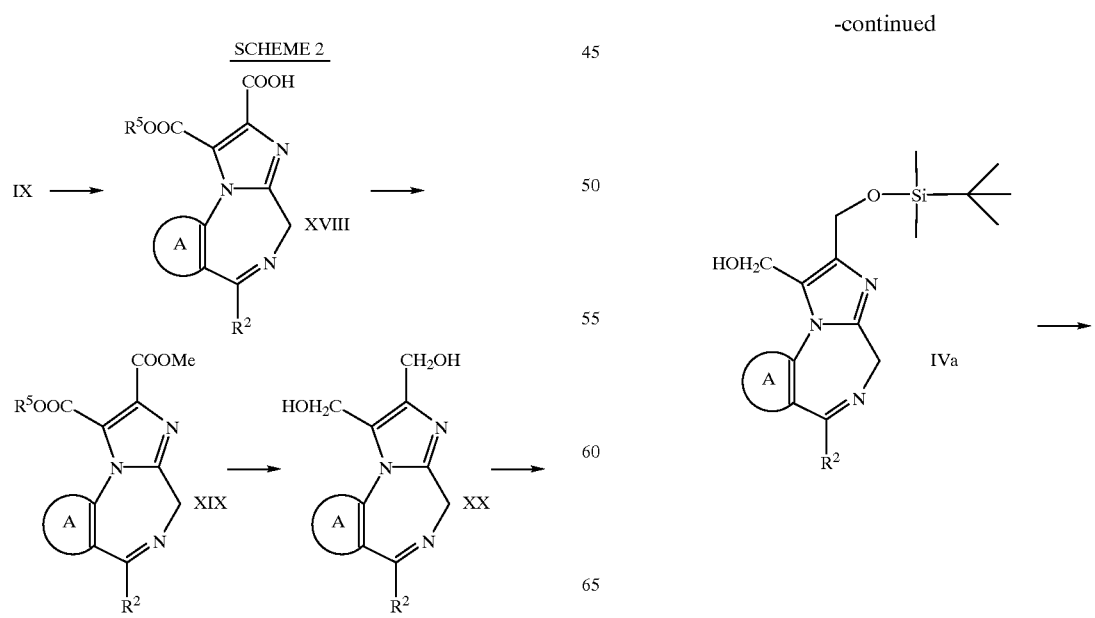

-continued

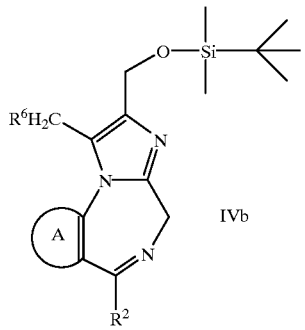

IVb

The compounds of general formulae IX and XIV have a central significance for the manufacture of the compounds of general formula I in accordance with the invention. They can be prepared in accordance with Scheme 1 by different routes. These possibilities are described in detail in Examples 1a, 1b, 1c, 3a, 3b, 4, 14a, 14b, 15a, 16a, 17a, 18a, 19a, 19b, 20a, 20b, 20c and 20d. The compounds of general formulae IX and XIV are known compounds and are described in J. Med. Chem., 1971, 14, 1978–1081; Am. Chem. Soc., 1953, 75, 6244; Yakugaku Zasshi, 1973, 93, 1253–1262; J. Chem. Res. Synop., 1980, 400; J. Med. Chem., 1991, 34, 1209; J. Med. Chem., 1980, 23, 392–402; DE-OS 2 233 483.

The preparation of a compounds of formula IIIa starting from a compound of general formula IX will be described in more detail on the basis of an example in which A and $R^2$ have the above significance and Alk signifies ethyl.

A corresponding diazepine of general formula IX is treated in succession with N-ethyldiisopropylamine and ethyl bromopyruvate (Ex. 18), dissolved in tetrahydrofuran, while warming for several minutes, cooled, treated with diethyl ether and the resulting N-ethyldiisopropylamine hydrobromide is filtered off. The filtrate was subsequently converted into the target compounds of formula IIIa according to known methods.

Compounds of general formula IIa are obtained in accordance with Scheme 1 by reacting a compound of general formula IX with 1,3-dichloroacetone in the presence of sodium bicarbonate. This reaction is conveniently effected in an inert solvent, such as e.g. dioxan under a protective gas atmosphere at room temperature.

Compounds of general formula IIb are obtained in an analogous manner. A compound of general formula IX is reacted with 1,3-dichloroacetone in the presence of anhydrous potassium carbonate or sodium hydrogen carbonate in dioxan and subsequently worked up according to known methods.

Compounds of general formula V are obtained starting from compounds of general formula XIV by reacting a diazepine of general formula XIV with 3,3-diethoxy-1-hydroxy-2-propylamine, dissolved in an alcohol, for example in butanol. This is conveniently effected within several hours while warming.

Also set forth in Scheme 1 is a process variant which leads over several steps to the preparation of compounds of general formula IIIb.

Compounds of general formula XV are obtained starting from a compound of general formula XIV by alkylation. Methyl iodide is a suitable alkylating agent; however, other alkylating agents are also possible.

This is conveniently carried out by boiling a compound of general formula XIV in the presence of potassium carbonate and the alkylating agent dissolved in a suitable solvent, e.g. acetone, at reflux while stirring. After working up has been effected the compound of formula V is converted with L-threonine alkyl ester hydrochloride, dissolved in pyridine, into compounds of formula XVI. This compound is obtained as a diastereomer mixture, which is converted without purification into compounds of general formula XVII. For this purpose, this compound, dissolved in dichloromethane, is added dropwise to a solution which is prepared as follows: a solution consisting of trifluoroacetic anhydride in dichloromethane is added dropwise to a cooled solution of dimethyl sulphoxide and dichloromethane and this mixture is subsequently treated with a compound of general formula XVI. The compounds of general formula XVII obtained are subsequently cyclized to compounds of general formula IIIb. This is conveniently carried out in dimethylformamide in the presence of p-toluenesulphonic acid monohydrate while warming.

Scheme 2 shows the preparation of compounds of general formula IVb starting from compounds of general formula IX. This is conveniently carried out as follows: a compound of general formula IX is reacted in the presence of dimethyl dihydroxyfumarate and triphenylphosphine, dissolved in tetrahydrofuran, with diethyl azodicarboxylate, dissolved in tetrahydrofuran, while cooling. After working up the resulting compound of general formula XVIII is conveniently dissolved in tetrahydrofuran and treated with oxalyl chloride in the presence of dimethylformamide. The thus-obtained acid chloride is converted into XIX by methanolysis. XIX is subsequently reduced to compounds of general formula XX. This is conveniently carried out according to generally known methods. Lithium aluminium hydride in tetrahydrofuran is especially well suited as the reducing agent. After reduction has been carried out the OH group at which no further reaction should take place is protected. Conveniently, for this purpose the corresponding diazepine of general formula XX is reacted with tert-butyldimethylsilyl chloride at room temperature in the presence of imidazole, dissolved in dimethylformamide. The resulting compound of general formula IVa can subsequently be converted with suitable activating agents, for example tetrabromomethane, and triphenylphosphine, into reactive compounds of general formula IVb for further reactions according to generally know methods.

A detailed description of the compounds prepared in Scheme 2 is given in Examples 6a, 6b, 6c, 6d, 6e, 7, 8 and 9.

As mentioned earlier, the compounds of formula I are novel. They have valuable pharmacodynamic properties and have only a low toxicity. They have as a common feature a pronounced affinity to the central benzodiazepine receptors and have pronounced anxiolytic, anticonvulsant, muscle relaxant and sedative-hypnotic properties on the basis of their agonistic activity at these receptors. They form acid addition salts which have a very good solubility in water and are therefore primarily suitable for the production of aqueous injection solutions.

The affinity of compounds of general formula I to the central benzodiazepine receptors was established in vitro according to the methods described in Nature 294, 763–765 (1981) and J. Neurochemistry 37, 714–722 (1981). According to these methods the inhibition of the binding of tritiated flumazenil to the specific benzodiazepine receptors in the cortex of rats by the respective test substances is determined. The $IC_{50}$ ("50% inhibiting concentration") denotes that concentration of the respective test substance which brings about a 50 percent inhibition of the specific binding of tritiated flumazenil to the specific benzodiazepine receptors in the cortex of rats.

The sedative/muscle relaxant properties of the compounds of formula II in accordance with the invention can be determined, for example, in the rotating rod test. Mice weighing 19–21 g are used for this test. They have free access to feed and drinking water up to 1 hour prior to the beginning of the test. They are brought into the test laboratory at least 30 minutes prior to the test. In the rotating rod test the animals are placed on a horizontally arranged, smooth metal rod having a diameter of 3 cm., which is rotated at 2 revolutions per minute. Initially, the animals are given the opportunity of familiarizing themselves with the test situation for 30 seconds. Subsequently, those animals which succeed in remaining on the rod for at least 1 minute are selected. The test preparations are then administered intraveneously to these animals in different dosages. At various points in time it is then determined whether the animals are able to remain for a minimum period on the rod (minimum period: 10 seconds, 1 minute from 5 minutes after administration). That dosage at which 50% of the animals are capable of remaining on the rod is determined ($ED_{50}$).

The results which have been obtained with representative members of the class of compound defined by general formula I in the tests described previously are compiled in the following Table.

H  6-(2-Fluorophenyl)-8-iodo-4H-imidazo[1,2-a][1,4] benzodiazepine-2 methanol
I  8-Bromo-6-(2-pyridyl)-4H-imidazo[1,2-a][1,4] benzodiazepine-2 methanol From the above Table it will be evident that compounds A to I display a sedative activity which sets in very rapidly and lasts only a relatively short time.

Having regard to their agonistic activity at the benzodiazepine receptors the compounds of formula I can be used as sedatives/hypnotics, anticonvulsants, muscle relaxants and anxiolytics. They are suitable, for example, as rapid but short acting hypnotics for peroral administration, especially—in the form of aqueous solutions of their acid addition salts—as injectable short acting hypnotics for premedication, sedation as well as narcosis induction and narcosis maintenance; preferred possibilities for use are thus premedication prior to narcosis induction, basal sedation prior to diagnostic or surgical intervention with or without local anaesthesia, long term sedation in intensive care, use as an induction agent for inhalation narcosis or as a sleep-inducing component of combination narcosis (including total intravenous anaesthesia) etc.

The compounds of formula I and pharmaceutically acceptable acid addition salts thereof can be used as medicaments, e.g. in the form of pharmaceutical preparations. The pharmaceutical preparations can be administered

TABLE

| Compound Example | Affinity to benzo-diazepine-receptors $IC_{50}$[nmol] | Rotating rod, test, $ED_{50}$ in mg/kg; i.v., determed at the following points in time after Administration ||||||||
|---|---|---|---|---|---|---|---|---|---|
| | | Mimimun time:10 ||| Minimum time:60 sec |||||
| | | 15 sec. | 30 sec. | 60 sec. | 2 min | 5 min | 15 min | 30 min | 60 min |
| A 1f, 2 | 2.6 | 0.5 | 0,7 | 0.6 | 1.2 | 2.3 | 5.3 | ≧10 | >10 |
| B 1g | 6.0 | 0.6 | 0,7 | 1.2 | 1.0 | ≧10 | ≧10 | ≧10 | >10 |
| C 4b, 10b | 1.7 | 0.1 | 0,3 | 0.3 | ≧10 | 0.8 | 0.4 | 1.1 | ≧10 |
| D 9 | 5.6 | 2.5 | 3,0 | 3.2 | 3.2 | 2.1 | 1.8 | ≧10 | >10 |
| E 11 | 1.2 | ≦0.32 | 0,4 | 0.5 | 3.2 | 0.9 | 0.5 | ≧3.2 | ≧3.2 |
| F 13 | 12.0 | 1.0 | 1,1 | 1.1 | >3.2 | 1.0 | 0.9 | 1.1 | 1.8 |
| G 14c | 2.3 | 0.2 | 0,2 | 0.3 | 0.3 | 0.1 | 0.2 | 0.2 | ≧1 |
| H 17b | 2.07 | 0.1 | 0.06 | 0.09 | 0.1 | 0.1 | 0.1 | ≧1 | >1 |
| I 18c | 40 | 1.5 | 2.0 | 3.0 | >10 | 1.4 | 1.8 | 3.0 | ≧10 |

Significances in this are:
A  2-Chloro-4-(2-fluorophenyl)-8,9-dihydro-6H-imidazo[1,2-a]thieno[3,2-f][1,4]diazepine-8-methanol
B  Methyl[2-chloro-4-(2-fluorophenyl)-8,9-dihydro-6H-imidazo[1,2-a]thieno[3,2-f]diazepin-8-y]acetate
C  8-Chloro-6-(2-fluorophenyl)-4H-imidazo[1,2-a] benzodiazepine-2-methanol
D  1-Allylaminomethyl-8-chloro-6-(2-fluorophenyl)-4H-imidazo[1,2-a][1,4]benzodiazepine-2-methanol
E  8-Chloro-6-(2-chlorophenyl)-4H-imidazo[1,2-a][1,4] benzodiazepine-2 methanol
F  8-Trifluoromethyl-6-phenyl-4H-imidazo[1,2-a][1,4] benzodiazepine-2 methanol
G  6-(2-Fluorophenyl)-8-nitro-4H-imidazo[1,2-a][1,4] benzodiazepine-2 methanol orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and pharmaceutically acceptable acid addition salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble acid addition salts of compound of formula I, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or a pharmaceutically acceptable acid addition salt thereof and a therapeutically inert excipient are also an object of the present invention, furthermore also a process for the production of such medicaments which is characterized by bringing one or more compounds of formula I or pharmaceutically acceptable acid addition salts thereof and, if desired, one or more other therapeutically valuable substances into a galenical administration form together with one [or] more therapeutically inert carriers.

As mentioned earlier, the compounds of formula I and pharmaceutically acceptable acid addition salts thereof can be used in accordance with the invention for therapeutic purposes, especially for anxiolytic and/or anticonvulsant and/or muscle relaxant and/or sedative-hypnotic purposes. The dosage can vary within wide limits and will, of course, be fitted to the individual requirements in each particular case. In general, in the case of intravenous administration a daily dosage of about 1 mg to 1000 mg should be appropriate. Finally, as mentioned earlier, the use of compounds of formula I and of pharmaceutically usable acid addition salts thereof for the production of medicaments, especially of anxiolytic and/or anticonvulsant and/or muscle relaxing and/or sedative-hypnotic medicaments, is also an object of the invention.

The following Examples are intended to illustrate the present invention in more detail, but do not limit its scope in any manner.

EXAMPLE 1

Manufacture of 2-chloro-4-(2-fluoro-phenyl)-8.9-dihydro-6H-imidazo[1,2-a]thieno[3,2-f][1,4]diazepine-8-methanol a) A suspension of 100 g of dihydrogen-hexachloro-stannate bis(thiophen-2-ylamine), 50.7 g of 2-fluorobenzonitrile and 54.7 g of aluminium. chloride (anhydrous) in 380 ml of 1,2-dichloroethane and 750 ml of toluene was stirred at room temperature while gassing with nitrogen for 0.5 h. and treated cautiously with 380 ml of boron trichloride (1M in xylene). The reaction mixture was stirred at 65° C. for 1 h. and at 110° C. for 5 h. The solution was poured into 1300 ml of ammonia (16% in methanol), 1000 ml of dichloromethane and ice, subsequently filtered through Hyflo. The organic phase was washed with saturated sodium chloride solution, dried with sodium sulphate, filtered and evaporated to dryness in a vacuum. The residue, 73 g of crude 3-[(2-fluoro-phenyl)-imino-methyl]-thiophen-2-ylamine was used as the starting product for the step described below without further purification.

b) A solution of 73 g of 3-[(2-fluoro-phenyl)-imino-methyl]-thiophen-2-ylamine and 48 g of aminoacetonitrile hydrochloride in 1150 ml of methanol was stirred at 75° C. under argon for 1 h. The reaction mixture was extracted with water/dichloromethane. The dichloromethane extracts were dried over sodium sulphate, filtered and evaporated to dryness in a vacuum. The residue (70 g) [(2-amino-thiophen-3-yl)-(2-fluoro-phenyl)-methyleneamino]acetonitrile was used as the starting product for the step described below.

c) A solution of 70 g of [(2-amino-thiophen-3-yl)-(2-fluoro-phenyl)-methyleneamino]acetonitrile in 980 ml of acetic acid was stirred at 65° C. under argon for 1.5 h. After cooling the solvent was removed in a vacuum, the residue was dissolved in dichloromethane and neutralized with sodium bicarbonate solution while cooling with ice and extracted. The dichloromethane extracts were dried with sodium sulphate, filtered and evaporated to dryness in a vacuum. After crystallization from dichloromethane there were obtained 17.1 g of 5-(2-fluoro-phenyl)-3H-thieno[2,3-e][1,4]diazepin-2-ylamine of m.p. 219–220° C. (dec.).

d) 19 g of 5-(2-fluoro-phenyl)-3H-thieno[2,3-e][1,4]diazepin-2-ylamine were dissolved in 730 ml of 5% methanol in dichloromethane, treated while stirring well with 327 g of a 2.8% solution of chlorine gas in 5% methanol in dichloromethane and stirred at room temperature under argon for 5 minutes. Thereafter, the reaction mixture was poured into 600 ml of 0.2N sodium hydroxide solution while cooling with ice and extracted. The dichloromethane extracts were dried with sodium sulphate, filtered and the solvent was evaporated in a vacuum. After two fold boiling of the residue in 5% methanol in dichloromethane and filtration there were obtained 7.4 g of 7-chloro-5-(2-fluoro-phenyl)-3H-thieno[2,3-e][1,4]diazepin-2-ylamine of m.p. 215–217° C. (dec.).

e) A suspension of 9.5 g of 7-chloro-5-(2-fluoro-phenyl)-3H-thieno[2,3-e][1,4]diazepin-2-ylamine, 4.8 g of 1,3-dichloroacetone, 31.5 g of sodium bicarbonate in 220 ml of dioxan was stirred at room temperature under argon for 48 h. Thereafter, the temperature was increased to 80° C. and the reaction mixture was stirred under argon for a further 24 h. After cooling the suspension to 60° C. the crude (RS)-2-chloro-8-chloromethyl-4-(2-fluoro-phenyl)-8,9-dihydro-6H-imidazo[1,2-a]thieno[3,2-f][1,4]diazepin-8-ol was used without working up and purification for the step described below.

f) 37.2 g of 2.5N sodium hydroxide solution were added at 60° C. to a suspension of the reaction mixture (RS)-2-chloro-8-chloromethyl-4-(2-fluoro-phenyl)-8,9-dihydro-6H-imidazo[1,2-a]thieno[3,2-f][1,4]diazepin-8-ol obtained in accordance with paragraph e) and stirred under argon for 21 h., subsequently two 18.7 g portions of 2.5N sodium hydroxide solution were added at intervals of two hours and the mixture was stirred for 2 h. The suspension was extracted with sodium chloride solution saturated with dichloro methane in the presence of a small amount of methanol. The dichloromethane extracts were dried with sodium sulphate, filtered and evaporated to dryness in a vacuum. After crystallization of the residue from 5% methanol in dichloromethane 3.3 g of the starting product of step e) were recovered. The mother liquors were evaporated to dryness in a vacuum and the residue was chromatographed on 800 g of silica gel. With 5% methanol in dichloromethane there were eluted 1.5 g of 2-chloro-4-(2-fluoro-phenyl)-8,9-dihydro-6 6H-imidazo[1,2-a]thieno-[3,2-f][1,4]diazepine-8-methanol which was used without further purification as the starting product for the step described below.

Manufacture of methy-2-chloro-4-(2-fluoro-phenyl)-8,9-dihydro-6H-imidazo[1,2-a]thieno[3,2-f][1,4]diazepin-8-yl-acetate hydrochloride g) 31 drops of perchloric acid (70%) were added to a suspension of 1.5 g of 2-chloro-4-(2-fluoro-phenyl)-8,9- dihydro-6H-imidazo[1,2-a]thieno-[3,2-f][1,4]diazepine-8-methanol in 31 ml of acetic anhydride until the starting product was completely in solution. After stirring at room temperature for 20 min. the solution was poured into sodium carbonate/ice/dichloromethane and stirred at room temperature for 1 h. After extraction the dichloromethane extracts were dried with sodium sulphate, filtered and evaporated to dryness in a vacuum. The residue was dried in a high vacuum for 2 h., dissolved in 30 ml of acetone, treated with 52 g of 1.6% hydrochloric acid gas in diethyl ether, evaporated in a vacuum (223 mbar) and crystallized from acetone. After crystallization from acetone there was obtained 1 g of methyl[2-chloro-4-(2-fluoro-phenyl)-8,9-dihydro-6H-imidazo[1,2-a]thieno[3,2-f][1,4]diazepin-8-yl-acetate-hydrochloride of m.p. 126–129° C. (dec., strongly hygroscopic).

EXAMPLE 2

Manufacture of 2-chloro-4-(2-fluoro-phenyl)-8,9-dihydro-6H-imidazo[1,2-a]thieno[3,2-f][1,4]diazepine-8-methanol hydrochloride A solution of 450 mg of methyl (2-chloro-4-(2-fluoro-phenyl)-8,9-dihydro-6H-imidazo[1,2-a]diazepin-8-ylacetate)ester in 15 ml of methanol was treated with 3 ml of 3.5% sodium methanolate solution in methanol and stirred at room temperature under argon for 15 min. The solution was acidified with acetic acid and neutralized with a saturated sodium bicarbonate solution while cooling with ice. Subsequently, the reaction mixture was extracted with dichloromethane. The dichloromethane extract were dried with sodium sulphate, filtered and evaporated to dryness in a vacuum. The residue was dissolved in 15 ml of dichloromethane, treated with 27.6 g of 1.5% hydrochloric acid gas in methanol and evaporated in a vacuum (223 mbar). The residue was crystallized from acetone. There were obtained 243 mg of 2-chloro-4-(2-fluorophenyl)-8,9-dihydro-6H-imidazo[1,2-a]thieno[3,2-f][1,4]diazepine-8-methanol hydrochloride of m.p. 142–145° C. (dec., strongly hygroscopic).

EXAMPLE 3

Manufacture of 4-phenyl-6H-imidazo[1,2-a]thieno[2,3-f][1,4]diazepine-8-methanol dihydrochloride a) 5.46 g of potassium tert-butylate were added to a solution of 8.82 g of 5-phenyl-2,3-dihydro-1H-thieno[3,2-e][1,4]diazepin-2-one in 600 ml of anhydrous tetrahydrofuran and the solution was stirred at room temperature for 1 h. and at 50° C. for 1 h. After cooling a solution of 12.72 g of dimorpholin-4-yl-phosphine chloride in 300 ml of anhydrous tetrahydrofuran and the reaction mixture was stirred at room temperature for 20 min. The solution was poured into sodium bicarbonate/ice/dichloromethane, extracted, the dichloromethane extracts were dried with sodium sulphate, filtered and the organic phase was evaporated to dryness in a vacuum. After crystallization of the residue from diethyl ether/dichloromethane 2 g of the starting product were recovered. The mother liquors were concentrated and the residue (dimorpholin-4-yl-phosphinic acid 5-phenyl-3H-thieno[3,2-e][1,4]-diazepin-2-yl ester) was used without further purification as the starting product for the step described below.
b) Gaseous ammonia was conducted into a solution of 14.4 g of dimorpholin-4-yl-phosphinic acid (5-phenyl-3H-thieno[3,2-e][1,4]-diazepin-2-yl) ester at room temperature while stirring until the starting product had reacted completely. After removal of the solvent in a vacuum the residue was extracted with dichloromethane/water in the presence of a small amount of methanol. The aqueous phase was washed several times with dichloromethane, the dichloromethane extracts were dried with sodium sulphate, filtered and evaporated in a vacuum. The residue was suspended in dichloromethane and stirred for 0.5 h. There were obtained 2.9 g of crude 5-phenyl-3H-thieno[3,2-e][1,4]diazepin-2-ylamine which was used without further purification as the starting product for the step described below.
c) A suspension of 2.9 g of 5-phenyl-3H-thieno[3,2-e][1,4]diazepin-2-ylamine, 11.7 g of sodium bicarbonate and 1.83 g of 1,3-dichloroacetone in 80 ml of dioxan was stirred at room temperature under argon for 48 h. Thereafter, the temperature of the reaction mixture was increased to 80° C. and the suspension was stirred under argon for a further 27 h. After cooling to 60° C. 19.2 g of 2.5N sodium hydroxide solution were added and the reaction mixture was stirred under argon for a further 20 h. Subsequently, a further two 19.2 g portions of 2.5N sodium hydroxide solution were added at intervals of twenty hours. The suspension was extracted with dichloromethane/saturated sodium chloride solution in the presence of a small amount of methanol. The dichloromethane extracts were dried with sodium sulphate, filtered and evaporated in a vacuum. The residue was suspended twice in succession in methanol and triturated. There were obtained 2.14 g of crude 4-phenyl-6H-imidazo[1,2-a]thieno[2,3-f][1,4]diazepin-8-ylmethanol which was used without further purification as the free base for the preparation of the dihydrochloride.

200 mg of crude 4-phenyl-6H-imidazo[1,2-a]thieno[2,3-f][1,4]-diazepin-8-ylmethanol were dissolved in hot methanol, filtered while hot and treated with 30 g of 1.5% hydrochloric acid in methanol and evaporated in a vacuum (223 mbar). The residue was crystallized from methanol. There was obtained 4-phenyl-6H-imidazo[1,2-a]thieno-[2,3-f][1,4]diazepine-8-methanol dihydrochloride of m.p. >230° C.

EXAMPLE 4

Manufacture of 8-chloro-6-(2-fluorophenyl)-4H-imidazo[1,2-a][1,4]benzodiazepine-2-methanol a) 800 ml of aqueous ammonia solution (25%) were added to a solution of 27.6 g of 7-chloro-5-(2-fluorophenyl)-3H-1,4-benzodiazepine-2(1H)-thione (J. B. Hester jr., A. D. Rudzik and B. V. Bharat, J.Med. Chem., 1971, 14, 1078–1081) in 900 ml of tetrahydrofuran and the mixture was stirred intensively at room temperature for 72 h. The separated organic phase was concentrated in a vacuum to about 50 ml and the crystals which thereby separated were filtered off. Drying was carried out in a vacuum at 50° C., firstly over calcium chloride, then over phosphorus pentoxide. There were obtained 22.8 g (87%) of 7-chloro-5-(2-fluorophenyl)-3H-1,4-benzodiazepin-2-ylamine as a pale yellow crystalline powder of m.p. 248–249° C. (dec.) which was used without further purification for the steps described below.
b) A suspension of 20.0 g of 7-chloro-5-(2-fluorophenyl)-3H-1,4-benzodiazepin-2-ylamine and 9.72 g of 1,3-dichloroacetone in 300 ml of dioxan was treated with 5.84 g of sodium hydrogen carbonate and heated at reflux for 6 h. Then, 160 ml of 1N aqueous sodium hydroxide solution were added dropwise and the mixture was boiled for a further hour. The reaction mixture was concentrated in a vacuum to a large extent, treated with water and extracted three times with equal volumes of dichloromethane. The combined organic phases were dried over magnesium sulphate, concentrated in a vacuum and chromatographed over 1 kg of silica gel. With dichloromethane containing 5% methanol there were obtained 11.3 g of the desired product which was recrystallized from ethyl acetate/diisopropyl ether. There were thus obtained 10.5 g (44%) of 8-chloro-6-(2-fluorophenyl)-4H-imidazo[1,2-a][1,4]benzodiazepine-2-methanol of m.p. 199–201° C.

EXAMPLE 5

Manufacture of 8-chloro-6-(2-fluorophenyl)-1-methyl-4H-imidazo[1,2-a][1,4]benzodiazepine-2-methanol a) A suspension of 120 g of 7-chloro-5-(2-fluorophenyl)-3H-1,4-benzodiazepine-2(1H)-thione (J. B. Hester jr., A. D. Rudzik and B. V. Bharat, J.Med. Chem., 1971, 14, 1078–1081), 150 g of potassium carbonate and 300 ml of iodomethane in 2.6 l of acetone was heated at reflux while stirring intensively for 3 h. The precipitate was filtered off and the filtrate was concentrated in a vacuum to about ⅓ of the original volume. 500 ml of diethyl ether were added while stirring and the precipitate was filtered off. The filtrate was concentrated to dryness and then treated with sufficient acetone such that all passed into solution (about 300 ml). 1.5 l of hexane were added dropwise while stirring intensively, precipitate 7-chloro-5-(2-fluorophenyl)-2-methylthio-3H-1,4-benzodiazepine was filtered off, the filtrate was concentrated in a vacuum and, after drying in a vacuum at 50° C., 39.2 g were isolated. From the concentrated mother liquors there were isolated after chromatographic purification on 500-g of silica gel with ethyl acetate/hexane 1:3 a further 17.6 g (total yield 45%) of the desired product. This was used without further purification for the step described below.

b) A solution of 22.0 g of 7-chloro-5-(2-fluorophenyl)-2-methylthio-3H-1,4-benzodiazepine and 20.0 g of L-threonine methyl ester hydrochloride in 200 ml of pyridine was stirred at 75° C. for 5 h. The solvent was removed in a vacuum and the residue was purified by chromatography on 800 g of silica gel with dichloromethane containing 5% methanol. There were obtained 16.3 g (59%) of methyl 2-[7-chloro-5-(2-fluorophenyl)-3H-1,4-benzodiazepin-2-ylamino]-3-hydroxy-butyrate as a diastereomer mixture which was used without further purification as the starting product for the step described below.

c) A solution of 3.8 ml of trifluoroacetic acid anhydride in 7.3 ml of dichloromethane was added dropwise to a solution, cooled with dry ice/acetone, of 2.7 ml of dimethyl sulphoxide in 18 ml of dichloromethane was added in such a manner that the temperature did not exceed −55° C. After stirring in the cold for 30 min. a solution of 7.54 g of methyl 2-[7-chloro-5-(2-fluorophenyl)-3H-1,4-benzodiazepin-2-ylamino]-3-hydroxybutyrate in 15 ml of dichloromethane was added dropwise in a manner such that the temperature did not exceed −60° C. The mixture was stirred in a dry ice bath for 2 h., then brought to −30° C. for 5 min. and subsequently again cooled in a dry ice bath. After the slow addition of 7.5 ml of triethylamine the mixture was stirred, firstly in the cold for a further 30 min., then at room temperature for 30 min. For the working up the mixture was extracted with 30 ml of water. The organic phase was dried over magnesium sulphate, concentrated in a vacuum and purified by chromatography on 350 g of silica gel. Byproducts were eluted with dichloromethane containing 1% methanol. With dichloromethane containing 3% methanol there were isolated 5.56 g (74%) of methyl 2-[7-chloro-5-(2-fluorophenyl)-3H-1,4-benzodiazepin-2-ylamino]-3-oxo-butyrate which was used without further purification for the step described below.

d) 1.40 g of methyl 2-[7-chloro-5-(2-fluorophenyl)-3H-1,4-benzodiazepin-2-ylamino]-3-oxo-butyrate were taken up in 10 ml of dimethylformamide, 100 mg of p-toluenesulphonic acid monohydrate were added and the mixture was stirred at 80° C. for 2 h. For the working up the mixture was treated with 30 ml of water and extracted 5 times with 50 ml of diethyl ether each time. The combined organic phases were dried over magnesium sulphate, concentrated in a vacuum and purified by chromatography on 70 g of silica gel with dichloromethane containing 2% methanol. There were obtained 550 mg (41%) of methyl 8-chloro-6-(2-fluorophenyl)-1-methyl-4H-imidazo[1,2-a][1,4]benzodiazepine-2-carboxylate of m.p. 137–138° C. which was used without further purification for the step described below.

e) 3.3 ml of a 1M lithium aluminium, hydride solution in tetrahydrofuran was cooled to −75° C. and a solution of 1.26 g of methyl 8-chloro -6-(2-fluorophenyl)-1-methyl-4H-imidazo[1,2-a][1,4]benzodiazepine-2-carboxylate in 15 ml of tetrahydrofuran was added dropwise. After 1 h. in a dry ice/acetone bath the mixture was brought to 0° C. and left for a further h. For the working up, 0.1 ml of water was added dropwise at 0° C. while stirring intensively, 0.1 ml of 15% sodium hydroxide solution was added after 5 min., finally 0.3 ml of water was added after a further 10 min. After 12 h. the mixture was filtered, the residue was suspended in 100 ml of methanol, stirred well for 1 h. and filtered. The combined filtrates were concentrated in a vacuum and purified by chromatography on 80 g of silica gel with dichloromethane containing 5% methanol. There were obtained 234 mg (20%) of 8-chloro-6-(2-fluoro-phenyl)-1-methyl-4H-imidazo[1,2-a][1,4]benzodiazepine-2-methanol. For the preparation of the methanesulphonic acid salt, 230 mg of this product were dissolved in 10 ml of dichloromethane and 6.0 ml of a 0.1M methanesulphonic acid solution in diethyl ether were slowly added dropwise. After removal of the solvent in a vacuum the residue was taken up in 10 ml of water, filtered and lyophilized. There were isolated 183 mg of hygroscopic 8-chloro-6-(2-fluorophenyl)-1-methyl-4H-imidazo-[1,2-a][1,4]benzodiazepine-2-methanol methanesulphonate (1:2) of m.p. 116° C.

EXAMPLE 6

Manufacture of 8-chloro-1-diethylaminomethyl-6-(2-fluorophenyl)-4H-imidazo[1,2-a][1,4]benzodiazepine-2-methanol hydrochloride (1:1)

a) A suspension of 17.3 g of 7-chloro-5-(2-fluorophenyl)-3H-1,4-benzodiazepin-2-ylamine, 15.3 g of dimethyl dihydroxyfumarate (E. F. Hartree, J. Am. Chem. Soc., 1953, 75, 6244) and 45.6 g of triphenylphosphine in 350 ml of tetrahydrofuran was cooled to 0° C. and a solution of 26.8 ml of diethyl azodicarboxylate in 50 ml of tetrahydrofuran was slowly added dropwise. The mixture was stirred in the cold for a further 2 h., then stirred at room temperature for 10 h. Then, a further 5.0 ml of diethyl azodicarboxylate, 10.0 g of triphenylphosphine and 5.0 g of dimethyl dihydroxyfumarate were added at room temperature, the mixture was stirred for 2 h. and finally heated under reflux for 5 h. The solvent was removed in a vacuum, the oily residue was taken up in 500 ml of methanol and, after the addition of 200 ml of 1N sodium hydroxide solution, stirred for 5 days. For the working up, the methanol was removed at 40° C. to a large extent and the residue was extracted with 300 ml of ethyl acetate. The aqueous phase was brought to pH 3 with 10% aqueous hydrochloric acid and the precipitate which separated was filtered off, dried and there were thus isolated 16.2 g (66%) of 8-chloro-6-(2-fluorophenyl)-4H-imidazo[1,2-a][1,4]benzodiazepine-1,2 dicarboxylic acid 1-methyl ester. This was used without further purification as the starting product for the step described below.

b) 13.0 g of 8-chloro-6-(2-fluorophenyl)-4H-imidazo[1,2-a][1,4]-benzodiazepine-1,2-dicarboxylic acid 1-methyl ester were taken up in 100 ml of tetrahydrofuran, 1 ml of dimethylformamide was added and 7.0 ml of oxalyl chloride were slowly added dropwise at 0° C. After the completion of the addition the mixture was stirred at room temperature for a further 30 min. Then, a mixture of 25 ml of pyridine and 25 ml of methanol were added dropwise while cooling in such a manner that the temperature did not exceed 10° C. Subsequently, the mixture was stirred at room temperature for a further 1 h. For the working up, all volatiles were removed in an oil pump vacuum, the residue was taken up with 200 ml of dichloromethane and extracted with 200 ml of water. The organic phase was dried over magnesium sulphate, concentrated in a vacuum and brought to crystallization by trituration with diethyl ether. After drying in a high vacuum at 50° C. there were thus obtained 12.1 g (90%) of dimethyl 8-chloro-6-(2-fluorophenyl)-4H-imidazo[1,2-a][1,4]-benzodiazepine-1,2-dicarboxylate of m.p. 206–207° C. which was used directly without further purification for the next step.

c) A solution of 7.29 g of dimethyl 8-chloro-6-(2-fluorophenyl)-4H-imidazo[1,2-a][1,4]benzodiazepine-1,2-dicarboxylate in 100 ml of tetrahydrofuran was cooled to −78° C. and 20 ml of a 1M lithium aluminium hydride solution in tetrahydrofuran was added dropwise in a manner such that the temperature did not exceed −70° C. After completion of the addition the mixture was brought slowly to room temperature and stirred for 1 h. Then, it was treated dropwise with saturated sodium potassium tartrate solution and stirred well for 12 h. The insoluble material was filtered off, the filtrate was concentrated and the residue was recrystallized from isopropanol. The concentrated mother liquor was purified by chromatography on 300 g of silica gel with dichloromethane/methanol/glacial acetic acid 90:10:2 and the fractions containing the product, after removal of the solvent, were again recrystallized from isopropanol. There were thus isolated a total of 4.1 g (65%) of [8-chloro-6-(2-fluorophenyl)-2-hydroxymethyl-4H-imidazo[1,2-a]-[1,4]benzodiazepin-1-yl]-methanol of m.p. 222° C.

d) A solution of 7.29 g of tert-butyldimethylsilyl chloride in 15 ml of dimethyl formamide was added dropwise to a solution, cooled to 0° C., of 15.0 g of [8-chloro-6-(2-fluorophenyl)-2-hydroxymethyl-4H-imidazo[1,2-a]-[1,4]benzodiazepin-1-yl]-methanol and 3.29 g of imidazole in 50 ml of dimethyl formamide. The mixture was brought to room temperature and stirred at room temperature for 12 h. For the working up, the solvent was removed in an oil pump vacuum at 40° C. and the residue was taken up with 500 ml of water and 500 ml of dichloromethane. The aqueous phase was again extracted with equal volumes of dichloromethane and the combined organic phases were dried over magnesium sulphate. After removal of the solvent in a vacuum the residue remaining behind was purified by chromatography on 500 g of silica gel with a dichloromethane/methanol mixture 98:2. After recrystallization from diethyl ether/hexane there were thus obtained 14.4 g (74%) of 2-(tert-butyl-dimethyl-silanyloxymethyl)-8-chloro-6-(2-fluorophenyl)-4H-imidazo[1,2-a][1,4]benzodiazepine-1-methanol of m.p. 172° C. This was used without further purification as the starting product for the steps described below.

e) 820 mg of tetrabromomethane and 650 mg of triphenylphosphine were added in succession and portionwise to a solution of 1.0 g of 2-(tert-butyl-dimethyl-silanyloxymethyl)-8-chloro-6-(2-fluorophenyl)-4H-imidazo[1,2-a][1,4]benzodiazepine-1-methanol in 10 ml of tetrahydrofuran. After stirring at room temperature for 2 h. a further 160 mg of tetrabromomethane and 130 mg of triphenylphosphine were added and the mixture was stirred for a further 2 h. Subsequently, the solvent was removed at 40° C. in a vacuum and the residue was triturated twice with 10 ml of ethyl acetate each time and filtered off. 2.0 ml of diethylamine were added to the combined filtrates and this reaction mixture was stirred at 50° C. for 10 h. Then, all volatiles were removed in an oil pump vacuum at 40° C., the residue was taken up with 5 ml of tetrahydrofuran and 10 ml of 1N hydrochloric acid and stirred at room temperature for 3 h. After the addition of 30 ml of ethyl acetate the separated organic phase was again extracted with 10 ml of 1N hydrochloric acid. The combined aqueous phases were treated with 10 ml of 2N sodium hydroxide solution and extracted three times with 30 ml of ethyl acetate each time. Drying of the organic phase over magnesium sulphate and removal of the solvent in a vacuum left behind 850 mg of crude product which was purified by chromatography on 80 g of silica gel with a mixture of dichloromethane/methanol/ammonium hydroxide 140:10:1. There were thus obtained 740 mg (84%) of 8-chloro-1-diethylaminomethyl-6-(2-fluorophenyl)-4H-imidazo[1,2-a][1,4]benzodiazepine-2-methanol as a crystalline foam. The m.p. lay at 159° C. after recrystallization from diethyl ether. For the preparation of the hydrochloride, 280 mg of this product were dissolved in 10 ml of dioxan and 6.23 ml of 0.1N hydrochloric acid were added dropwise. The mixture was lyophilized, taken up with 10 ml of water, filtered and again lyophilized and there was thus obtained 8-chloro-1-diethylaminomethyl-6-(2-fluorophenyl)-4H-imidazo[1,2-a][1,4]benzodiazepine-2-methanol hydrochloride (1:1) of m.p. 130° C. (dec.).

EXAMPLE 7

Manufacture of 8-chloro-6-(2-fluorophenyl)-1-morpholin-4-ylmethyl-4H-imidazo[1,2-a][1,4]benzodiazepine-2-methanol hydrochloride (1:1)

820 mg of tetrabromomethane and 650 mg of triphenylphosphine were added in succession and portionwise to a solution of 1.0 g of [2-(tert.-butyl-dimethylsilanyloxymethyl)-8-chloro-6-(2-fluorophenyl)-4H-imidazo[1,2-a][1,4]benzodiazepin-1-yl]-methanol in 10 ml of tetrahydrofuran. After stirring at room temperature for 2 h. a further 160 mg of tetrabromomethane and 130 mg of triphenylphosphine were added and the mixture was stirred for a further 2 h. Subsequently, the solvent was removed at 40° C. in a vacuum, the residue was triturated twice with 10 ml of ethyl acetate each time and filtered off. 2.0 ml of morpholine were added to the combined filtrates and this reaction mixture was stirred at 50° C. for 2 h., then all volatiles were removed in an oil pump vacuum at 40° C., the residue was taken up with 5 ml of tetrahydrofuran and 10 ml of 1N hydrochloric acid and stirred at room temperature for 3 h. After the addition of 30 ml of ethyl acetate the separated organic phase was again extracted with 10 ml of 1N hydrochloric acid. The combined aqueous phases were treated with 10 ml of 2N sodium hydroxide solution and extracted three times with 30 ml of ethyl acetate each time. Drying of the organic phase over magnesium sulphate and removal of the solvent in a vacuum yielded 800 mg of crude product which was purified by chromatography on 50 g of silica gel with a mixture of dichloromethane/methanol/ammonium hydroxide 140:10:1. There were thus isolated 560 mg (62%)

of 8-chloro-6-(2-fluorophenyl)-1-morpholin-4-ylmethyl-4H-imidazo[1,2-a][1,4]benzodiazepine-2-methanol as a crystalline foam. After recrystallization from dichloromethane/diethyl ether the m.p. lay at 216° C. For the preparation of the hydrochloride, 243 mg (0.551 mmol) of this product were dissolved in 10 ml of dioxan and 5.22 ml of 0.1N hydrochloric acid were added dropwise. The mixture was lyophilized, taken up with 10 ml of water, filtered and again lyophilized and there was thus obtained 8-chloro-6-(2-fluorophenyl)-1-morpholin-4-ylmethyl-4H-imidazo[1,2-a][1,4]benzodiazepine-2-methanol hydrochloride (1:1) of m.p. 155° C. (dec.).

EXAMPLE 8

Manufacture of 8-chloro-6-(2-fluorophenyl)-1-methylaminomethyl-4H-imidazo[1,2-a][1,4]benzodiazepine-2-methanol hydrochloride (1:1)

820 mg of tetrabromomethane and 650 mg of triphenylphosphine were added in succession and portionwise to a solution of 1.0 g of [2-(tert.-butyl-dimethyl-silanyloxymethyl)-8-chloro-6-(2-fluorophenyl)-4H-imidazo[1,2-a][1,4]benzodiazepin-1-yl]methanol in 10 ml of tetrahydrofuran. After stirring at room temperature for 2 h. a further 160 mg of tetrabromomethane and 130 mg of triphenylphosphine were added and the mixture was stirred for a further 2 h. Subsequently, the solvent was removed at 40° C. in a vacuum and the residue was triturated twice with 10 ml of ethyl acetate each time and filtered off. The combined filtrates were added to 50 ml of a tetrahydrofuran solution saturated with methylamine at 0° C. and this reaction mixture was stirred at room temperature for 3 h. Then, all volatiles were removed in an oil pump vacuum at 40° C., the residue was taken up with 5 ml of tetrahydrofuran and 10 ml of 1N hydrochloric acid and stirred at room temperature for 3 h. After the addition of 30 ml of ethyl acetate the separated organic phase was again extracted with 10 ml of 1N hydrochloric acid. The combined aqueous phases were treated with 10 ml of 2N sodium hydroxide solution and extracted three times with 30 ml of ethyl acetate each time. Drying of the organic phase over magnesium sulphate and removal of the solvent in a vacuum yielded 600 mg of crude product which was purified by chromatography on 50 g of silica gel with a mixture of dichloromethane/ methanol/ammonium hydroxide 200:10:1. 290 mg (37%) of 8-chloro-6-(2-fluorophenyl)-1-methylaminomethyl-4H-imidazo[1,2-a][1,4]benzodiazepine-2-methanol were isolated as a crystalline foam. After recrystallization from dichloromethane/diethyl ether the m.p. lay at 172° C. For the preparation of the hydrochloride, 196 mg (0.509 mmol) of this product were dissolved in 5 ml of dioxan and 4.85 ml of 0.1N hydrochloric acid were added dropwise. The mixture was lyophilized, taken up with 20 ml of water, filtered and again lyophilized and there was thus isolated 8-chloro-6-(2-fluorophenyl)-1-methylaminomethyl-4H-imidazo[1,2-a][1,4]benzodiazepine-2-methanol hydrochloride (1:1) of m.p. 1500° C. (dec.).

EXAMPLE 9

Manufacture of 1-allylaminomethyl-8-chloro-6-(2-fluorophenyl)-4H-imidazo[1,2-a][1,4]benzodiazepine-2-methanol hydrochloride (1:1)

3.07 g of tetrabromomethane and 2.43 g (9.3 mmol) of triphenylphosphine were added in succession and portionwise to a solution of 3.0 g of [2-(tert.-butyl-dimethylsilanyloxymethyl)-8-chloro-6-(2-fluoro-phenyl)-4H-imidazo[1,2-a][1,4]benzodiazepin-1-yl]methanol in 10 ml of tetrahydrofuran. After stirring at room temperature for 3 h. the mixture was filtered and the residue was rinsed with a small amount of tetrahydrofuran. 25 ml (333 mmol) of allylamine were added to the filtrate and this reaction mixture was stirred at 50° C. for 2 h. Then, all volatiles were removed at 40° C. in an oil pump vacuum, the residue was taken up with 30 ml of tetrahydrofuran and 30 ml of 1N hydrochloric acid and stirred at room temperature for 3 h. After the addition of 100 ml of ethyl acetate the separated organic phase was again extracted with 30 ml of 1N hydrochloric acid. The combined aqueous phases were treated with 30 ml of 2N sodium hydroxide solution and extracted three times with 100 ml of ethyl acetate each time. Drying of the organic phase over magnesium sulphate and removal of the solvent in a vacuum yielded 2.6 g of crude product which was purified by chromatography on 300 g of silica gel with a mixture of dichloromethane/methanol/ammonium hydroxide 200:10:1. 1.96 g (77%) of 1-allylaminomethyl-8-chloro-6-(2-fluorophenyl)-4H-imidazo [1,2-a][1,4]benzodiazepine-2-methanol were thus isolated as a crystalline foam. After recrystallization from dichloromethane/diethyl ether the melting point lay at 173° C. For the preparation of the hydrochloride, 776 mg of this product were dissolved in 30 ml of dioxan and 18.9 ml of 0.1N hydrochloric acid were added dropwise. The mixture was lyophilized, taken up with 10 ml of water, filtered, again lyophilized and there was thus obtained 1-allylaminomethyl-8-chloro-6-(2-fluorophenyl)-4H-imidazo[1,2-a][1,4]benzodiazepine-2-methanol hydrochloride (1:1) of m.p. 140° C.

EXAMPLE 10

Manufacture of 8-chloro-6-(2-fluorophenyl)-4H-imidazo[1,2-a][1,4]benzodiazepine-2-methanol a) To a suspension of 32.3 g of 7-chloro-5-(2-fluorophenyl)-3H-1,4-benzodiazepine-2(1H)-thione (J. B. Hester jr., A. D. Rudzik and B. V. Bharat, J-Med. Chem., 1971, 14, 1078–1081) in 900 ml of butanol were added 17.2 g of 3,3-diethoxy-1-hydroxy-2-propylamine (S. David and A. Veyrieres, Carbohyd. Res. 1969, 10, 35–38) and the mixture was heated at reflux while stirring for 24 h. The solvent was then removed in a vacuum. The residue (55 g of red oil) was dissolved in a 1:1 mixture of ethyl acetate and hexane and chromatographed over 700 g of silica gel. With ethyl acetate/hexane 1:1 and 3:1 there were firstly eluted about 8 g of a byproduct and then with ethyl acetate/hexane 9:1 30.8 g of 7-chloro-2-(3,3-diethoxy-1-hydroxy-2-propylamino)-5-(2-fluorophenyl)-3H-1,4-benzodiazepine which was used without further purification as the starting product for the step described below.

b) A solution of 30 g of 7-chloro-2-(3,3-diethoxy-1-hydroxy-2-propyl-amino)-5-(2-fluorophenyl)-3H-1,4-benzodiazepine in 300 ml of glacial acetic acid was heated to reflux temperature for 5 h. After cooling the solvent was removed in a vacuum, the residue was taken up in 300 ml of ethanol, the solution was treated with 150 ml of 2N aqueous sodium hydroxide solution and left te stand at room temperature for 2 h. Then, about 200 ml of ethanol were distilled off at 30° C. in a vacuum. The solution remaining behind was extracted three times with chloroform. The chloroform extracts were washed with saturated sodium chloride solution, then dried over sodium sulphate and evaporated to dryness in a vacuum. The residue (20.5 g) was dissolved in chloroform and chromatographed over 500 g of silica gel. Byproducts (total 4.1 g) were eluted with chloroform containing 0.2% to 1.6% ethanol. 13.0 g of the desired product were eluted with chloroform containing 2.4 to 20% ethanol. After recrystallization from ethyl acetate/diethyl ether there were obtained 11.6 g of 8-chloro-6-(2-fluorophenyl)-4H-imidazo[1,2-a][1,4]benzodiazepine-2-methanol of m.p. 196–199.5° C. After repeated recrystallization from ethyl acetate the m.p. lay at 199–201° C.

EXAMPLE 11

Manufacture of 8-chloro-6-(2-chlorophenyl)-4H-imidazo[1,2-a][1,4]benzodiazepine-2-methanol A solution of 9.1 g of 2-amino-7-chloro-5-(2-chlorophenyl)-3H-1,4-benzodiazepine (K. Meguro, H. Tawada & Y. Kuwada, Yakugaku Zasshi, 1973, 93, 1253–1262) and 11.4 g of 1,3-dichloroacetone in 195 ml of dioxan was treated with 24.9 g of anhydrous potassium carbonate and stirred at 98° C. for 22 h. After cooling the inorganic salts were filtered off, the filtrate was treated with 0.75 g of p-toluenesulphonic acid and stirred at 98° C. for 2.5 h. 60 ml of 1N aqueous sodium hydroxide solution and 2.0 g of active charcoal were added to this solution and the mixture was stirred at 80° C. for 2.5 h. After cooling the mixture was filtered and the filtrate was concentrated in a vacuum. The residue was taken up in 300 ml of dichloromethane and the solution was shaken with 200 ml of 6N aqueous hydrochloric acid. The crystals which thereby separated were filtered off (4.2 g) and the filtrate was extracted a further three times with 200 ml of 6N aqueous hydrochloric acid each time The combined aqueous extracts were made weakly basic (pH 8 to 9) with aqueous sodium hydroxide solution and the precipitate was filtered off. The filter cake together with the crystals (4.2 g) filtered off earlier were taken up in chloroform and in 2N aqueous sodium hydroxide solution, the mixture was filtered clear and the aqueous phase is extracted a further twice with chloroform. The chloroform extracts were dried over sodium sulphate, concentrated in a vacuum to 100 ml and chromatographed over 210 g of silica gel. A small amount of byproduct was eluted with chloroform. The desired product was eluted with chloroform containing 1 to 4% ethanol and was crystallized from ethyl acetate. There were obtained 3.8 g of 8-chloro-6-(2-chlorophenyl)-4H-imidazo-[1,2-a][1,4]benzodiazepine-2-methanol of m.p. 174–175° C., which was converted into the hydrochloride, m.p. 257–259° C.

EXAMPLE 12

Manufacture of 8-chloro-6-phenyl-4H-imidazo[1,2-a][1,4]benzodiazepine-2-methanol A solution of 10.9 g of 2-amino-7-chloro-5-phenyl-3H-1,4-benzodiazepine (K. Meguro, H. Tawada & Y. Kuwada, Yakugaku Zasshi, 1973, 93, 1253–1262) and 5.2 g of 1,3-dichloroacetone in 200 ml of dioxan was treated with 3.13 g of anhydrous sodium hydrogen carbonate and stirred at 98° C. for 22 h. After cooling the inorganic salts were filtered off, the filtrate was treated with 0.93 g of p-toluenesulphonic acid and stirred at 98° C. for 1.5 h. 74.5 ml of 1N aqueous sodium hydroxide solution and 2.5 g of active charcoal were added to this solution and the mixture was stirred at 80° C. for 2 h. After cooling the mixture was filtered over Dicalite and the filtrate was concentrated in a vacuum. The residue was taken up in dichloromethane and water and the aqueous phase was extracted four times with chloroform. The chloroform was evaporated in a vacuum. The residue (about 8 g) was crystallized from ethyl acetate. The crystals (7.3 g) were filtered off, dissolved in dichloromethane and chromatographed over 180 g of silica gel. The desired product was eluted with dichloromethane containing 2 to 4% ethanol and was recrystallized from ethyl acetate/ethanol 2:1. There were obtained 3.4 g of 8-chloro-6-phenyl-4H-imidazo[1,2-a][1,4]benzodiazepine-2-methanol of m.p. 203–204° C., which was converted into the hydrochloride, m.p. 252–254° C.

EXAMPLE 13

Manufacture of 8-trifluoromethyl-6-phenyl-4H-imidazo[1,2-a][1,4]benzodiazepine-2-methanol A solution of 10.5 g of 2-amino-7-trifluoromethyl-5-phenyl-3H-1,4-benzodiazepine (K. Meguro, H. Tawada & Y. Kuwada, Yakugaku Zasshi, 1973, 93, 1253–1262) and 4.84 g of 1,3-dichloroacetone in 220 ml of dioxan was treated with 2.72 g of anhydrous sodium hydrogen carbonate and stirred at 98° C. for 16 h. After cooling the inorganic salts were filtered off, the filtrate was treated with 0.75 g of p-toluenesulphonic acid and stirred at 98° C. for 2 h. 60 ml of 1N aqueous sodium hydroxide solution were added to this solution and the mixture was stirred at 80° C. for 3 h. After cooling the mixture was concentrated in a vacuum. The residue was taken up in chloroform and water and the aqueous phase was extracted a further four times with chloroform. The chloroform was evaporated in a vacuum. The residue was recrystallized twice from ethyl acetate. There were obtained 3.15 g of 8-trifluoromethyl-6-phenyl-4H-imidazo[1,2-a][1,4]benzodiazepine-2-methanol of m.p. 193–194° C., which was converted into the hydrochloride of m.p. 252–254° C.

EXAMPLE 14

Manufacture of 6-(2-fluorophenyl)-8-nitro-4H-imidazo[1,2-a][1,4]benzodiazepine-2-methanol a) A solution of 20.0 g of 5-(2-fluorophenyl)-7-nitro-3H-1,4-benzodiazepin-2(1H)-one (G. M. Clarke, J. B. Lee, F. J. Swinbourne & B. Williamson, J. Chem. Res. Synop. 1980, 400) in 100 ml of hexamethylphosphoric acid triamide was treated with 14 g of Lawesson reagent and the mixture was stirred at 105° C. for 70 min. The reaction mixture was poured into 800 ml of saturated aqueous sodium hydrogen carbonate solution and 800 ml of water. After stirring at room temperature for 15 min. the precipitate was filtered off, washed with water and dried. There were obtained 20 g of crude 5-(2-fluorophenyl)-7-nitro-3H-1,4-benzodiazepine-2(1H)-thione, which was used in this form for the next step.

A sample of pure 5-(2-fluorophenyl)-7-nitro-3H-1,4-benzodiazepine-2(1H)-thione of m.p. 218–220° C. was obtained by the chromatography of 2 g of crude material over 50 g of silica gel, elution with dichloromethane and recrystallization from ethyl acetate.

b) 350 ml of 25% aqueous ammonia solution were added to a solution of 20 g of 5-(2-fluorophenyl)-7-nitro-3H-1,4-benzodiazepine-2(1H)-thione in 1 l of tetrahydrofuran. The solution was stirred at room temperature for 20 h. and then concentrated to 200 ml in a vacuum. The crystalline precipitate was filtered off (12.1 g) and the filtrate was concentrated to 50 ml. A further 3.1 g of crystals could be filtered off. Total yield 15.2 g of 2-amino-5-(2-fluorophenyl)-7-nitro-3H-1,4-benzodiazepine of m.p. 225–227° C.

c) A solution of 14.9 g of 2-amino-5-(2-fluorophenyl)-7-nitro-3H-1,4-benzodiazepine and 7.65 g of 1,3-dichloroacetone in 300 ml of dioxan was treated with 5.05 g of anhydrous sodium hydrogen carbonate and stirred at 98° C. for 16 h. A further 1.53 g of 1,3-dichloroacetone and 1.0 g of anhydrous sodium hydrogen carbonate were added and the mixture was stirred at 98° C. for a further 4 h. After cooling the inorganic salts were filtered off, the filtrate was treated with 1.5 g of p-toluenesulphonic acid and the mixture was stirred at 98° C. for 2 h. Then, the mixture was concentrated in a vacuum and the residue was partitioned between chloroform and water. The chloroform phase was washed with water, dried over sodium sulphate and evaporated in a vacuum. The oily residue was dissolved in dichloromethane and chromatographed over 600 g of silica gel. With dichloromethane/ethanol 99:1 there were eluted 13 g of oily 2-chloromethyl-6-(2-fluorophenyl)-8-nitro-4H-imidazo[1,2-a][1,4]benzodiazepine which was used for the next step.

The hydrochloride, m.p. 251–253° C., was obtained by reaction with anhydrous hydrochloric acid in ethyl acetate.

A solution of 12 g of 2-chloromethyl-6-(2-fluorophenyl)-8-nitro-4H-imidazo [1,2-a][1,4]benzodiazepine in 100 ml of dioxan was treated with a solution of 3.5 g of sodium carbonate in 50 ml of water and stirred at 80° C. for 2.5 h. Then, the mixture was made weakly acidic (pH 6 to 7) with aqueous 3N hydrochloric acid and evaporated in a vacuum. The residue was taken up in chloroform, washed twice with water, dried over sodium sulphate and evaporated in a vacuum. The residue was dissolved in chloroform and chromatographed over 250 g of silica gel. With chloroform/ethanol 98:2 there were isolated a small amount of impurities, with chloroform/,6thanol 98:2 there was eluted 6-(2-fluorophenyl)-8-nitro-4H-imidazo[1,2-a][1,4]benzodiazepine-2-methanol. After recrystallization from chloroform there were obtained 5.8 g of 6-(2-fluorophenyl)-8-nitro-4H-imidazo[1,2-a][1,4]benzodiazepine-2-methanol of m.p. 230–231° C. This was converted into the hydrochloride of m.p. 239–241° C.

EXAMPLE 15

Manufacture of 6-(2-chlorophenyl)-8-nitro-4H-imidazo[1,2-a][1,4]benzodiazepine-2-methanol a) To a solution of 14 g of 5-(2-chlorophenyl)-7-nitro-3H-1,4-benzodiazepine-2(1H)-thione (J. B. Hester, A. D. Rudzik & B. V. Kamdar, J. Med. Chem., 1971, 14, 1078–1081) in 700 ml of tetrahydrofuran were added firstly 260 ml of 25% aqueous ammonia solution and then 50 ml of methanol. The solution was stirred at room temperature for 20 h. and then concentrated to about 25 ml in a vacuum. The crystalline precipitate was filtered off and recrystallized from dioxan. There were obtained 13.2 g of 2-amino-5-(2-chlorophenyl)-7-nitro-3H-1,4-benzodiazepine of m.p. 222–224° C.

b) A solution of 3.14 g of 2-amino-5-(2-chlorophenyl)-7-nitro-3H-1,4benzodiazepine and 1.39 g of 1,3-dichloroacetone in 100 ml of dioxan was treated with 0.925 g of anhydrous sodium hydrogen carbonate and stirred at 98° C. for 20 h. Then, a further 0.28 g of 1,3 dichloroacetone and 0.23 g of anhydrous sodium hydrogen carbonate were added and the mixture was stirred at 98° C. for 3 h. After cooling the inorganic salts were filtered off, the filtrate was treated with 0.23 g of p-toluenesulphonic acid and stirred at 98° C. for 2 h. The solution was decolorized with active charcoal and filtered over Dicalite. The filtrate was concentrated in a vacuum, the residue was dissolved in dichloromethane and chromatographed over 65 g of silica gel. With dichloromethane there was eluted an impurity, with dichloromethane/ethanol 99:1 there were eluted 2.7 g of 2-chloromethyl-6-(2-chlorophenyl)-8-nitro-4H-imidazo[1,2-a][1,4]benzodiazepine which was used without further purification for the further reaction.

A solution of 2.7 g of 2-chloromethyl-6-(2-chlorophenyl)-8-nitro-4H-imidazo [1,2-a][1,4]benzodiazepine in 30 ml of dioxan was treated with a solution of 0.74 g of sodium hydrogen carbonate in 10 ml of water and the mixture was stirred at 80° C. for 2.5 h. The mixture was filtered and the filtrate was made neutral with aqueous 3N hydrochloric acid. The filtrate was evaporated in a vacuum and the residue was taken up in chloroform and water. The chloroform phase was washed with water, dried over sodium sulphate and evaporated in a vacuum. The residue was crystallized in 30 ml of ethyl acetate and diethyl ether and filtered. The crystals were dissolved in dichloromethane and chromatographed over 75 g of silica gel. With dichloromethane/ ethanol 99:1, 98:2 and 97:3 there were eluted small amounts of different impurities, with dichloromethane/ethanol 95:5 there was eluted 6-(2-chlorophenyl)-8-nitro-4H-imidazo[1,2-a][1,4] benzodiazepine-2-methanol. After recrystallization from ethyl acetate there were obtained 1.4 g of pure 6-(2-chlorophenyl)-8-nitro-4H-imidazo[1,2-a][1,4] benzodiazepine-2-methanol of m.p. 173–174° C. which was converted into the methane-sulphonate (m.p. 211–212° C.).

EXAMPLE 16

Manufacture of 8-nitro-6-phenyl-4H-imidazo[1,2-a][1,4]benzodiazepine-2-methanol a) 300 ml of 25% aqueous ammonia solution were added to a solution of 16 g of 7-nitro-5-phenyl-3H-1,4-benzodiazepine-2(1H)-thione (J. B. Hester, A. D. Rudzik & B. V. Kamdar, J.Med.Chem., 1971, 14, 1078–1081) in 850 ml of tetrahydrofuran. The solution was stirred at room temperature for 20 h. and then concentrated to about 50 ml in a vacuum. The crystalline precipitate was filtered off and recrystallized from dioxan. There were obtained 8.0 g of 2-amino-7-nitro-5-phenyl-3H-1,4-benzodiazepine which was used in this form for the next step.

b) A solution of 8.0 g of 2-amino-7-nitro-5-phenyl-3H-1,4-benzodiazepine and 4.34 g of 1,3-dichloroacetone in 200 ml of dioxan was treated with 2.76 g of anhydrous sodium hydrogen carbonate and stirred at 98° C. for 20 h. Then, a further 0.28 g of 1,3-dichloroacetone and 0.23 g of anhydrous sodium hydrogen carbonate were added and the mixture was stirred at 980° C. for 3 h. After cooling the inorganic salts were filtered off, the filtrate was treated with 0.65 g of p-toluenesulphonic acid and stirred at 98° C. for 1 h. The solution was decolorized with active charcoal and filtered through Dicalite. The filtrate was concentrated in a vacuum, the residue was dissolved in chloroform, the chloroform extracts were washed three times with water, then dried over sodium sulphate and chromatographed over 500 g of silica gel. With dichloro methane there was eluted an impurity, with dichloromethane/ethanol 99:1 there were eluted 5.1 g of 2-chloromethyl-8-nitro-6-phenyl-4H-imidazo[1,2-a][1,4]benzodiazepine which was used without further purification for the further reaction.

A solution of 5.1 g of 2-chloromethyl-8-nitro-6-phenyl-4H-imidazo[1,2-a][1,4]benzodiazepine in 70 ml of dioxan was treated with a solution of 1.54 g of sodium hydrogen carbonate in 30 ml of water and the mixture was stirred at 80° C. for 2.5 h. The mixture was filtered and the filtrate was made weakly acidic (pH 6 to 7) with aqueous 3N hydrochloric acid. The filtrate was evaporated in a vacuum and the residue was taken up in chloroform and water. The chloroform phase was washed with water, dried over sodium sulphate and evaporated in a vacuum. The crystalline residue (3.2 g) was dissolved in chloroform and chromatographed over 130 g of silica gel. With chloroform and with chloroform/ethanol 98:2 there were eluted small amounts of various impurities, with chloroform/ethanol 97:3 and 96:4 there was eluted 8-nitro-6-phenyl-4H-imidazo[1,2-a][1,4]

benzodiazepine-2-methanol. After recrystallization from ethanol there were obtained 2.45 g of pure 8-nitro-6-phenyl-4H-imidazo[1,2-a][1,4]benzodiazepine-2-methanol of m.p. 250–251° C. which was converted into the hydrochloride (m.p. 295–297° C.).

EXAMPLE 17

Manufacture of 6-(2-fluorophenyl)-8-iodo-4H-imidazo[1,2-a][1,4]benzodiazepine-2-methanol a) 50 ml of 25% aqueous ammonia solution were added to a solution of 2.3 g of 5-(2-fluorophenyl)-7-iodo-3H-1,4-benzodiazepine-2(1H)-thione (A. Walser, T. Flynn, C. Mason, H. Crowley, C. Maresco, B. Yaremko & M. O'Donell, J.Med.Chem., 1991, 34, 1209) in 120 ml of tetrahydrofuran. After the addition of 5 ml of methanol the solution was stirred at room temperature for 24 h. and then evaporated in a vacuum. The residue was partitioned between saturated aqueous sodium hydrogen carbonate solution and chloroform. The aqueous phase was extracted a further three times with chloroform. The chloroform extracts were dried over sodium sulphate and evaporated in a vacuum. The residue was recrystallized from ethyl acetate. There were obtained 2.73 g of 2-amino -7-iodo-5-(2-fluorophenyl)-3H-1,4-benzodiazepine of m.p. 219–221° C.

b) A solution of 1.65 g of 2-amino-7-iodo-5-(2-fluorophenyl)-3H-1,4-benzodiazepine and 0.67 g of 1,3-dichloroacetone in 23 ml of dioxan was treated with 0.44 g of anhydrous sodium hydrogen carbonate and the mixture was stirred at 98° C. for 20 h. After cooling the inorganic salts were filtered off, the filtrate was treated with 0.35 g of p-toluenesulphonic acid and stirred at 98° C. for 2 h. The solution was decolorized with active charcoal and filtered over Dicalite. The filtrate was concentrated in a vacuum, the residue was dissolved in chloroform, the chloroform solution was washed three times with water, then dried over sodium sulphate and chromatographed over 50 g of silica gel. With dichloromethane there was eluted an impurity, with dichloromethane/ethanol 99:1 there were eluted 1.2 g of 2-chloromethyl-6-(2-fluorophenyl)-8-iodo-4H-imidazo[1,2-a][1,4]benzodiazepine which was used without further purification for the further reaction.

A solution of 1.2 g of 2-chloromethyl-6-(2-fluorophenyl)-8-iodo-4H-imidazo [1,2-a][1,4]benzodiazepine in 20 ml of dioxan was treated with a solution of 0.4 g of sodium hydrogen carbonate in 10 ml of water and the mixture was stirred at 80° C. for 2 h. The mixture was filtered and the filtrate was made weakly acidic (pH 6 to 7) with aqueous 3N hydrochloric acid. The filtrate was evaporated in a vacuum and the residue was taken up in chloroform and water. The chloroform phase was washed with water, dried over sodium sulphate and evaporated in a vacuum. The residue was recrystallized from ethanol. There was obtained 0.6 g of amorphous 6-(2-fluorophenyl)-8-iodo-4H-imidazo[1,2-a][1,4]benzodiazepine-2-methanol which was converted into the crystalline hydrochloride (m.p. 274–276° C.),

EXAMPLE 18

Manufacture of 8-bromo-6-(2-pyridyl)-4H-imidazo [1,2-a][1,4]benzodiazepine-2-methanol a) 59.5 g of 7-bromo-5-(2-pyridyl)-3H-1,4-benzodiazepine-2(1H)-thione (J. B. Hester, jr., A. D. Rudzik & P.F . Von Voigtlander, J. Med. Chem., 1980,23, 392–402) in 800 ml of tetrahydrofuran were added to 1.0 l of 25% aqueous ammonia solution and 300 ml of methanol. The mixture was stirred at room temperature for 16 h., with the solution which formed being concentrated to about 500 ml in a vacuum. The crystals were filtered off, washed with water and dried. There were obtained 52 g of 2-amino-7-bromo-5-(2-pyridyl)-3H-1,4-benzodiazepine which was used without further purification for the next step. A sample recrystallized from dioxan melted at 213–215° C. (dec.).

b) A suspension of 52 g of 2-amino-7-bromo-5-(2-pyridyl)-3H-1,4-benzodiazepine in 1.5 l of tetrahydrofuran was treated in succession with 58 ml of N-ethyldiisopropylamine and 44 ml of ethyl bromopyruvate and the mixture was stirred at 65° C. for 20 min. Then, a further 5.8 ml of N-ethyldiisopropylamine and 44 ml of ethyl bromopyruvate were added and the mixture was stirred at 65° C. for a further 20 min. After cooling in an ice bath 0.5 l of diethyl ether was added and the crystals were filtered off. 49.5 g of N-ethyldiisopropylamine hydrobromide were obtained. The filtrate was evaporated in a vacuum, the residue was taken up in dichloromethane and shaken twice with saturated aqueous sodium hydrogen carbonate solution. The organic phase was dried over sodium sulphate and chromatographed over 2 kg of silica gel. With dichloromethane/ethanol 197:3 and 196:4 there were firstly eluted small amounts of impurities, then with dichloromethane/ethanol 97:3, 95:5 and 94:6 there were isolated a total of 58.2 g of ethyl 3-[2-amino-7-bromo-5-(2-pyridyl)-3H-1,4-benzodiazepin-1-yl]pyruvate. This was dissolved in 1 l of acetic acid and stirred at 100° C. for 3.5 h. The solution was then evaporated in a vacuum and the residue was partitioned between dichloromethane and saturated aqueous sodium hydrogen carbonate solution (1 l of each). The dichloromethane phase was separated, dried over sodium sulphate and chromatographed over 2 kg of silica gel. 17.2 g of ethyl 8-bromo-6-(2-pyridyl)-4H-imidazo[1,2-a][1,4]benzodiazepine-2-carboxylate were obtained as dark red crystals by elution with ethyl acetate. This was again chromatographed over 2 kg of silica gel. Strongly coloured impurities were eluted with ethyl acetate/dichloromethane 1:1 and 2:1. The desired ethyl 8-bromo-6-(2-pyridyl)-4H-imidazo[1,2-a][1,4]benzodiazepine-2-carboxylate was eluted with ethyl acetate. There were obtained 11.7 g of ethyl 8-bromo-6-(2-pyridyl)-4H-imidazo[1,2-a][1,4]benzodiazepine-2-carboxylate of m.p. 227–230° C.

c) 0.38 g of lithium aluminium hydride was added portionwise to a suspension of 2.06 g of ethyl 8-bromo-6-(2-pyridyl)-4H-imidazo[1,2-a][1,4]benzodiazepine-2-carboxylate in 250 ml of tetrahydrofuran at −40° C. while stirring vigorously. A dark green solution thereby formed and this was stirred at −7 to −10° C. for 45 min. Then, the mixture was cooled to −35° C. and treated dropwise with 2 ml of water. After stirring at room temperature for 2 h. a further 6.0 ml of water were added slowly. The reaction mixture was filtered clear over Dicalite and the filtrate was evaporated in a vacuum. The residue was partitioned between 100 ml of chloroform and 50 ml of saturated aqueous sodium hydrogen carbonate solution. The chloroform phase was separated, dried over sodium sulphate and evaporated in a vacuum. The residue (1.9 g) was dissolved in 100 ml of tert-butanol and 50 ml of pyridine, treated with 1.0 g of selenium dioxide and stirred at 65° C. for 30 min. The mixture was evaporated in a vacuum, the residue was dissolved in chloroform, with a small amount of insoluble impurity being filtered off. The solution was chromatographed over 250 g of aluminium oxide (activity 1). A small amount of impurity was eluted with dichloromethane/etanol 98:2, then 0.95 g of the desired 8-bromo-6-(2-pyridyl)-4H-imidazo[1,2-a][1,4]benzodiazepine-2-methanol was eluted with dichloromethane/ethanol 95:5, 90:10 and 80:20. After recrystallization from ethyl acetate there was obtained 0.80 g of 8-bromo-6-(2-pyridyl)-4H-imidazo[1,2-a][1,4]benzodiazepine-2-methanol of m.p. 176–178° C. which was converted into the hydrochloride (m.p. above 300° C.).

EXAMPLE 19

Manufacture of 8-chloro-6-(2-pyridyl)-4H-imidazo[1,2-a][1,4]benzodiazepine-2-methanol a) A solution of 18.5 g of 7-chloro-5-(2-pyridyl)-3H-1,4-benzodiazepin-2(1H)-one (N. Ch. Hindley, T. M. McClymont & G. O. Chase; F. Hoffmann La Roche and Co., A. G., German Offenlegungsschrift 2,233,483, 1973) in 150 ml of pyridine was treated with 14.2 g of Lawesson reagent and the mixture was stirred at 100° C. for 2 h. After the addition of 1.0 g of Lawesson reagent the mixture was stirred at 100° C. for a further 0.5 h. and then evaporated in a vacuum. The residue was poured into 500 ml of saturated aqueous sodium hydrogen carbonate solution and the precipitate was filtered off (22 g). The red crystals were suspended in 100 ml of boiling methanol. After cooling 100 ml of diethyl ether were added and the crystals were filtered off. There were obtained 18.7 g of 7-chloro-5-(2-pyridyl)-3H-1,4-benzodiazepine-2(1H)-thione of m.p. 217–218° C.

b) 300 ml of 25% aqueous ammonia solution and 100 ml of methanol were added to a solution of 18.5 g of 7-chloro-5-(2-pyridyl)-3H-1,4-benzodiazepine-2(1H)-thione in 800 ml of tetrahydrofuran. The mixture was stirred at room temperature for 17 h., with the solution which formed being concentrated to about 200 ml in a vacuum. The crystals were filtered off, washed with water and dried, stirred in 25 ml of dioxan at 100° C., cooled and filtered off. There were obtained 16.3 g of 2-amino-7-chloro-5-(2-pyridyl)-3H-1,4-benzodiazepine which was used without further purification for the next step. A sample recrystallized from dioxan melted at 213–215° C.

c) A solution of 16.3 g of 2-amino-7-chloro-5-(2-pyridyl)-3H-1,4-benzodiazepine and 8.4 g of 1,3-dichloroacetone in 600 ml of dioxan was treated with 5.6 g of anhydrous sodium hydrogen carbonate and stirred at 100°0 C. for 16 h. A further 0.84 g of dichloroacetone and 0.56 g of anhydrous sodium hydrogen carbonate were added and the mixture was stirred at 100° C. for a further 8 h. The mixture was evaporated in a vacuum and the residue was partitioned between chloroform and water. The aqueous phase was extracted twice with dichloromethane. The combined organic phases were evaporated in a vacuum. The residue was dissolved in dichloromethane and chromatographed over 800 g of silica gel. With dichloromethane/ethanol 197:3 there were eluted small amounts of impurities, with dichloromethane/ethanol 196:4 there were eluted 10.2 g of the desired product. After recrystallization from ethyl acetate there were obtained 9.0 g of 2-chloromethyl-8-chloro-6-(2-pyridyl)-4H-imidazo[1,2-a][1,4]benzodiazepine of m.p. 161° C.

d) A solution of 2.0 g of 2-chloromethyl-8-chloro-6-(2-pyridyl)-4H-imidazo[1,2-a][1,4]benzodiazepine in 50 ml of dioxan was treated with a solution of 0.62 g of sodium hydrogen carbonate in 18 ml of water and the mixture was stirred at 80° C. for 1.5 h. The mixture was evaporated in a vacuum. The residue was partitioned between dichloromethane and aqueous sodium hydrogen carbonate solution. The aqueous phase was extracted twice with dichloromethane. The dichloromethane extracts were dried over magnesium sulphate and chromatographed over 100 g of silica gel. 1.7 g of the desired product were eluted with dichloromethane/ethanol mixtures containing 8 to 12% ethanol. After recrystallization from ethyl acetate/diethyl (sic) ether there were obtained 1.65 g of 8-chloro-6-(2-pyridyl)-4H-imidazo[1,2-a][1,4]benzodiazepine-2-methanol of m.p. 206–207° C., which was converted into the hydrochloride (dec. above 300° C.).

EXAMPLE 20

Manufacture of 8-iodo-6-(2-pyridyl)-4H-imidazo[1,2-a][1,4]benzodiazepine-2-methanol a) To a suspension of 18.7 g of 2-(2-amino-5-iodobenzoyl)pyridine (R. I. Fryer, P. Zhang & R. Rios, Synth.Commun. 1993, 23, 985–992) in 760 ml of benzene were added 10.2 ml of bromoacetyl bromide and the mixture was heated to reflux temperature for 20 h. After cooling the crystals are filtered off and these are then stirred for 30 min. in a mixture of 3 l of saturated aqueous sodium hydrogen (sic) carbonate solution and 1 l of dichloromethane. The aqueous phase was separated and extracted again with dichloromethane. The dichloromethane solutions were dried over sodium sulphate and evaporated. The dark brown crystalline residue (25 g) was chromatographed over 400 g of silica gel. With toluene/ethyl acetate 8:1 there were eluted 19.1 g of the desired product which was recrystallized from ethanol/diethyl ether. There were obtained 17.6 g of 2-[2-(bromoacetylamino)-5-iodobenzoyl]-pyridine, which was used without further purification for the next step.

b) A solution of 5.4 g of hexamethylenetetramine in 400 ml of anhydrous ethanol was saturated, with gaseous ammonia. The solution was heated to 80° C. and 17.2 g of 2-[2-(bromoacetylamino)-5-iodobenzoyl]-pyridine were added portionwise. The latter passed slowly into solution; crystals separated after 30 min. at 80° C. The mixture was stirred at reflux temperature for 4 h. while introducing further ammonia. After cooling the crystals were filtered off. 11.2 g of yellow crystals were obtained. After evaporation of the filtrate the residue was taken up in water. The crystals were filtered off (1.3 g). Both crystallizates were recrystallized from ethanol. There were obtained 9.7 g of 7-iodo-5-(2-pyridyl)-3H-1,4-benzodiazepin-2(1H)-one, m.p. 251–252° C. (dec.).

c) A solution of 3.45 g of 7-iodo-5-(2-pyridyl)-3H-1,4-benzodiazepin-2(1H)-one in 80 ml of hexamethylphosphoric acid triamide (HMPT) was treated with 4.24 g of Lawesson reagent and the mixture was stirred at 105° C. for 3.5 h. The reaction mixture was poured into 600 ml of saturated aqueous sodium hydrogen carbonate solution and 2 l of water. After stirring at room temperature for 30 min. the precipitate was filtered off. There were obtained 3.0 g of crude, yellow 7-iodo-5-(2-pyridyl)-3H-1,4-benzodiazepine-2(1H)-thione, m.p. 242° C., which was used in this form for the next step.

d) 60 ml of 25% aqueous ammonia solution and 30 ml of methanol were added to a suspension of 3.0 g of 7-iodo-5-(2-pyridyl)-3H-1,4-benzodiazepine-2(1H)-thione in 200 ml of tetrahydrofuran. The mixture was stirred at room temperature for 16 h., with the solution which formed being concentrated to about 50 ml in a vacuum. The crystals were filtered off, washed with water, dried, stirred in 25 ml of dioxan at 100° C., cooled and filtered off. There were obtained 2.35 g of 2-amino-7-iodo-5-(2-pyridyl)-3H-1,4-benzodiazepine of m.p. 228–229° C.

e) A, solution of 2.3 g of 2-amino-7-iodo-5-(2-pyridyl)-3H-1,4-benzodiazepine and 0.87 g of 1,3-dichloroacetone in 65 ml of dioxan was treated with 0.6 g of anhydrous sodium hydrogen carbonate and the mixture was stirred at 100° C. for 24 h. A further 0.09 g of dichloroacetone and 0.06 g of anhydrous sodium hydrogen carbonate were added and the mixture was stirred at 100° C. for a further 5 h. The mixture was evaporated in a vacuum and the residue was partitioned between chloroform and saturated aqueous sodium hydrogen carbonate solution. The aqueous phase was extracted three times with chloroform. The chloroform extracts were dried over sodium sulphate and chromatographed over 200 g of silica gel. With dichloromethane/ethanol 197:3 there were eluted small amounts of impurities, with dichloromethane/ethanol 195:5 there were eluted 1.3 g of the desired product. After recrystallization from ethyl acetate there were obtained 1.21 g of 2-chloromethyl-8-iodo-6-(2-pyridyl)-4H-imidazo [1,2-a][1,4]benzodiazepine of m.p. 216° C. (dec.).

f) A solution of 1.15 g of 2-chloromethyl-8-iodo-6-(2-pyridyl)-4H-imidazo[1,2-a][1,4]benzodiazepine in 40 ml of dioxan was treated with a solution of 0.28 g of sodium hydrogen carbonate in 10 ml of water and stirred at 80° C. for 1.5 h. The mixture was evaporated in a vacuum. The residue was partitioned between chloroform and aqueous sodium hydrogen carbonate solution. The aqueous phase was extracted three times with chloroform. The chloroform extracts were dried over sodium sulphate, concentrated to 30 ml in a vacuum and chromatographed over 50 g of silica gel. 1.05 g of the desired product were eluted with chloroform/ethanol mixtures containing 3 to 7% ethanol. After recrystallization from ethyl acetate/diethyl ether there was obtained 0.955 g of 8-iodo-6-(2-pyridyl)-4H-imidazo[1,2-a][1,4]benzodiazepine-2-methanol of m.p. 206–207° C. which was converted into the hydrochloride (dec. above 300° C.).

EXAMPLE 21

Manufacture of 2-acetoxymethyl-8-chloro-6-(2-fluorophenyl)-4H-imidazo-[1,2-a][1,4]benzodiazepine 0.96 ml of acetic anhydride was added dropwise to a solution of 1.36 g of 8-chloro-6-(2-fluorophenyl)-4H-imidazo[1,2-a][1,4]benzodiazepine-2-methanol in 30 ml of pyridine. The reaction mixture was stirred at room temperature for 70 h. and then evaporated in a vacuum. The residue was treated with saturated aqueous sodium hydrogen carbonate solution and this was extracted twice with dichloromethane. The dichloromethane extracts were dried over sodium sulphate and the solution was chromatographed over 50 g of silica gel. 1.4 g of an oil were eluted with dichloromethane/ethanol 197:3 and this was crystallized from diethyl ether/diisopropyl ether. There were obtained 2.1 g of 2-acetoxymethyl-8-chloro-6-(2-fluorophenyl)-4H-imidazo [1,2-a][1,4]benzodiazepine of m.p. 134–136° C. which was converted into the hydrochloride.

What is claimed is:

1. A hydroxymethyl-imidazodiazepine compound of the formula

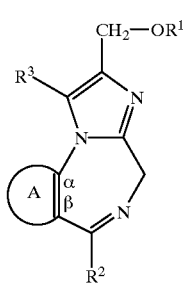

I wherein A and the two carbon atoms denoted by α and β together are one of the residues

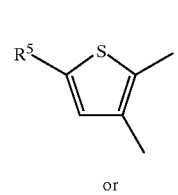

A² or

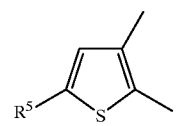

A³

$R^1$ is hydrogen or lower-alkanoyl;

$R^2$ is phenyl, o-halophenyl or 2-pyridyl;

$R^3$ is hydrogen, lower-alkyl, methylaminomethyl, allylaminomethyl or diethylaminomethyl;

$R^5$ is hydrogen or halogen, or pharmaceutical acceptable salts or esters thereof.

2. A compound according to claim 1, wherein A is residue $A^2$.

3. A compound according to claim 2, wherein $R^1$ is hydrogen or carbonylmethyl.

4. A compound according to claim 2, wherein $R^2$ is o-fluorophenyl.

5. A compound according to claim 2, wherein $R^3$ is hydrogen.

6. A compound according to claim 2, wherein $R^5$ is chlorine.

7. A compound according to claim 1, wherein A is residue $A^2$, $R^1$ is hydrogen or carbonylmethyl, $R^2$ is o-fluorophenyl, $R^3$ is hydrogen, and $R^5$ is chlorine.

8. A compound according to claim 7, wherein the compound is 2-chloro-4-(2-fluorophenyl)-8,9-dihydro-6H-imidazo[1,2-a]thieno[3,2-f][1,4]diazepine-8-methanol.

9. A compound according to claim 7, wherein the compound is methyl-[2-chloro-4-(2-fluorophenyl)-8,9-dihydro-6H-imidazo[1,2-a]thieno[3,2-f]diazepin-8-yl]acetate.

10. A pharmaceutical composition comprising an effective amount of a hydroxymethyl-imidazodiazepine compound of the formula

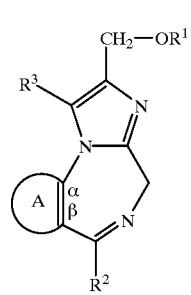

I wherein A and the two carbon atoms denoted by α and β together are one of the residues

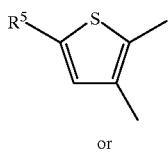
A² or

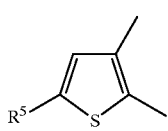
A³

R¹ is hydrogen or lower-alkanoyl;
R² is phenyl, o-halophenyl or 2-pyridyl;
R³ is hydrogen, lower-alkyl, methylaminomethyl, allylaminomethyl or diethylaminomethyl;
R⁵ is hydrogen or halogen,
or pharmaceutical acceptable salts and esters thereof;
or a pharmaceutically inert carrier.

11. A pharmaceutical composition according to claim 10, wherein A is residue $A^2$.

12. A pharmaceutical composition according to claim 11, wherein $R^1$ is hydrogen or carbonylmethyl.

13. A pharmaceutical composition according to claim 11, wherein $R^2$ is o-fluorophenyl.

14. A pharmaceutical composition according to claim 11, wherein $R^3$ is hydrogen.

15. A pharmaceutical composition according to claim 11, wherein $R^5$ is chlorine.

16. A pharmaceutical composition according to claim 10, wherein A is residue $A^2$, $R^1$ is hydrogen or carbonylmethyl, $R^2$ is o-fluorophenyl, $R^3$ is hydrogen, and $R^5$ is chlorine.

17. A pharmaceutical composition according to claim 16, wherein the compound is 2-chloro-4-(2-fluorophenyl)-8,9-dihydro-6H-imidazo[1,2-a]thieno[3,2-f][1,4]diazepine-8-methanol.

18. A pharmaceutical composition according to claim 16, wherein the compound is methyl-[2-chloro-4-(2-fluorophenyl)-8,9-dihydro-6H-imidazo[1,2-a]thieno[3,2-f]diazepin-8-yl]acetate.

\* \* \* \* \*